United States Patent [19]
Holland et al.

[11] Patent Number: 5,399,702
[45] Date of Patent: Mar. 21, 1995

[54] CYCLOALKYLTHIAZOLES

[75] Inventors: George W. Holland, North Caldwell; John R. Vermeulen, Wanaque; William J. Zally, Cresskill, all of N.J.

[73] Assignee: Hoffmann-La Roche Inc., Nutley, N.J.

[21] Appl. No.: 116,386

[22] Filed: Sep. 2, 1993

Related U.S. Application Data

[62] Division of Ser. No. 907,987, Jul. 2, 1992, Pat. No. 5,273,986.

[51] Int. Cl.$^6$ ............................................. C07D 277/22
[52] U.S. Cl. ................................... 548/119; 548/201; 548/204; 548/205; 548/202
[58] Field of Search ................ 548/119, 201, 202, 204, 548/205

[56] References Cited

U.S. PATENT DOCUMENTS

| | | | |
|---|---|---|---|
| 4,902,700 | 2/1990 | Hayashi et al. | 514/365 |
| 4,925,861 | 5/1990 | Hayashi et al. | 514/365 |
| 4,933,328 | 6/1990 | Curtze et al. | 514/92 |
| 5,001,140 | 3/1991 | Field et al. | 548/204 |

FOREIGN PATENT DOCUMENTS

| | | |
|---|---|---|
| 0219436 | 10/1986 | European Pat. Off. |
| 0287471 | 4/1988 | European Pat. Off. |
| 0318085 | 11/1988 | European Pat. Off. |
| 0355353 | 7/1989 | European Pat. Off. |
| 0469833 | 7/1991 | European Pat. Off. |
| 02169583 | 2/1991 | Japan. |

OTHER PUBLICATIONS

Tetrahedron vol. 44, No. 7, 1988 pp. 2021–2031.
Liebigs Annalen der Chemie No. 4, 1981 pp. 623–632.
Jpn.J.Pharmacol (1989) 50(1) 37–46.
Chemical Abstracts vol.114:6492f Preparation of 2-s-tyrylthiazole and benzothiazole derivatives as leukotriene antagonists (1991).

*Primary Examiner*—Mary C. Lee
*Assistant Examiner*—Jacqueline Haley
*Attorney, Agent, or Firm*—George M. Gould; George W. Johnston; Ellen Ciambrone Coletti

[57] ABSTRACT

Compounds of the formula:

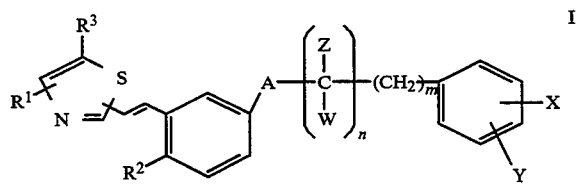

wherein the substituents are as defined herein, and enantiomers, diastereomers, racemates and salts with pharmaceutically acceptable bases, antagonize LTD$_4$ action and thus, are useful in treating bronchial asthma, pulmonary anaphylaxis, cystic fibrosis, chronic bronchitis, bronchiectasis, respiratory distress syndrome and pulmonary oedema.

4 Claims, No Drawings

CYCLOALKYLTHIAZOLES

This is a division of application Ser. No. 07/907,987, filed Jul. 2, 1992, now U.S. Pat. No. 5,273,986.

BRIEF SUMMARY OF THE INVENTION

The invention relates to compounds of the formula

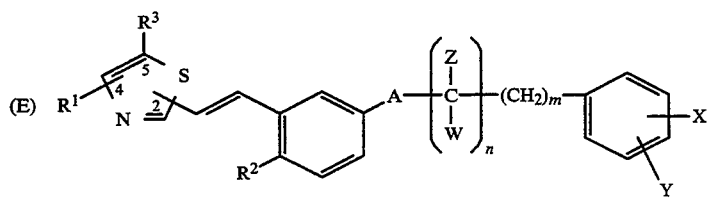

wherein $R^1$ is hydrogen, alkyl, cycloalkyl, carboxyl or alkoxycarbonyl;
$R^2$ is hydrogen, halogen or alkyl;
A is a group of the formula

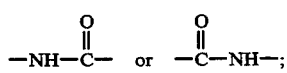

Z and W are independently hydrogen or alkyl or Z and W taken together are alkylene;
n is an integer of from 0–1;
m is an integer of from 0–3;
X is —CH$_2$OH or —R$^4$COR$^5$;
Y is halogen, alkoxy, acyloxy, hydroxy, alkyl, nitro, trifluoromethyl, hydrogen or cyano;
$R^3$ is hydrogen, alkyl or cycloalkyl;
$R^4$ is a direct bond or CH$_2$;
$R^5$ is hydroxy, alkoxy, NHR$^6$ or

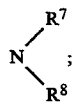

$R^6$ is hydrogen or alkyl; and
$R^7$ and $R^8$ are independently hydrogen or alkyl or $R^7$ and $R^8$ taken together are alkylene; provided that when m is 0 and n is 0, one of $R^1$ or $R^3$ is cycloalkyl, and their enantiomers, diastereomers, racemates and salts with pharmaceutically acceptable bases.

The compounds of formula I and pharmaceutically acceptable salts thereof antagonize peptidoleukotrienes (LTC$_4$, LTD$_4$, LTE$_4$), particularly leukotriene D$_4$ (LTD$_4$), and thus, are useful as bronchopulmonary agents, for example for the treatment of anaphylaxis, asthma and allergic reactions.

The compounds of formula I can also be used in combination with other antagonists of mediators of allergic reactions, such as antihistamines, platelet activating factor (PAF) antagonists, neurokinin antagonists, leukotriene B$_4$ (LTB$_4$) antagonists, and the like.

In another aspect, the invention relates to pharmaceutical compositions and methods of using the compound of formula I, and intermediates.

DETAILED DESCRIPTION OF THE INVENTION

The invention relates to compounds of the formula

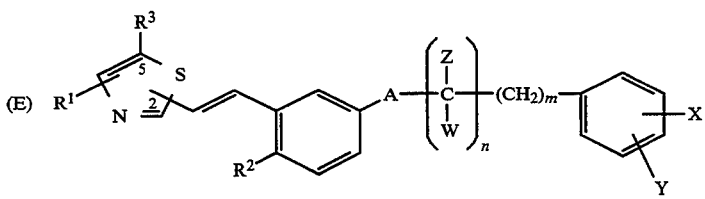

wherein $R^1$ is hydrogen, alkyl, cycloalkyl, carboxyl or alkoxycarbonyl;
$R^2$ is hydrogen, halogen or alkyl;
A is a group of the formula

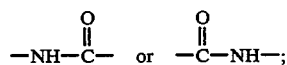

Z and W are independently hydrogen or alkyl or Z and W taken together are alkylene;
n is an integer of from 0–1;
m is an integer of from 0–3;
X is —CH$_2$OH or —R$^4$COR$^5$;
Y is halogen, alkoxy, acyloxy, hydroxy, alkyl, nitro, trifluoromethyl, hydrogen or cyano;
$R^3$ is hydrogen, alkyl or cycloalkyl;
$R^4$ is a direct bond or CH$_2$;
$R^5$ is hydroxy, alkoxy, NHR$^6$ or

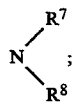

$R^6$ is hydrogen or alkyl; and
$R^7$ and $R^8$ are independently hydrogen or alkyl or $R^7$ and $R^8$ taken together are alkylene, provided that when m is 0 and n is 0, one of $R^1$ or $R^3$ is cycloalkyl, and their enantiomers, diastereomers, racemates and salts with pharmaceutically acceptable bases.

As used herein, the term "alkyl" preferably denotes a straight or branched chain saturated hydrocarbon containing 1 to 7 carbon atoms, for example, methyl, ethyl, propyl, isopropyl, butyl, t-butyl, neopentyl, pentyl, heptyl and the like.

The term "cycloalkyl" denotes a cyclic alkyl group of 3 to 8 carbon atoms, for example cyclopropyl, cyclopentyl, cyclohexyl and the like. The term "halogen" denotes chlorine, bromine, iodine and fluorine.

The term "alkoxy" alone or in combination, denotes an alkyl ether group, wherein alkyl is as previously described for example, methoxy, ethoxy, propoxy, isopropoxy, butoxy and the like.

A preferred group of the compounds of formula I are those wherein one of $R^1$ or $R^3$ is cycloalkyl.

A preferred group of the compounds of formula I are those wherein $R^1$ is cycloalkyl, especially 4-cyclobutyl; $R^2$ is hydrogen, A is

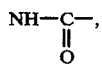

n is 0, X is carboxyl, Y is hydrogen, m is 1, $R^5$ is hydroxy and $R^3$ is hydrogen.

Especially preferred compounds of formula I are those wherein X is 2-carboxyl. $R^1$ and $R^3$ are preferably attached to the 4 and 5 positions, respectively, of the thiazolyl ring.

A preferred group of the compounds of formula I are those of the formula

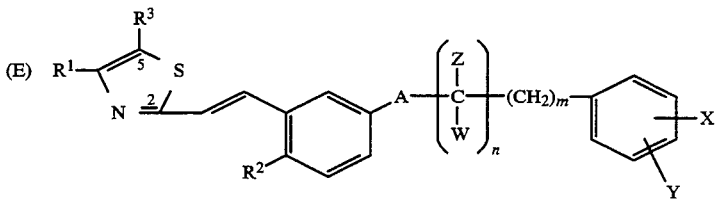 IH wherein $R^1$, $R^2$, A, Z, W, n, m, X, Y, $R^3$, $R^4$, $R^5$, $R^6$, $R^7$ and $R^8$ are as described above.

Preferred compounds of formula I of the invention are:

(E)-2-[2-[3-[2-[4-(1-methylethyl)-2-thiazolyl]ethenyl]phenylamino]-2-oxoethyl]benzoic acid;
(E)-2-[2-[3-[2-[4-(cyclopropyl)-2-thiazolyl]ethenyl]phenylamino]-2-oxoethyl]benzoic acid;
(E)-5-acetoxy-2-[2-[3-[2-[4-(cyclobutyl)-2-thiazolyl]ethenyl]phenylamino]-2-oxoethyl]benzoic acid;
(E)-2-[2-[3-[2-[4-(cyclobutyl)-2-thiazolyl]ethenyl]phenylamino]-2-oxoethyl]benzoic acid;
(E)-2-[2-[3-[2-[4-(cyclobutyl)-2-thiazolyl]ethenyl]phenylamino]-2-oxoethyl]benzoic acid methyl ester;
(E)-2-[2-[3-[2-[4-(cyclobutyl)-2-thiazolyl]ethenyl]phenylamino]-2-oxoethyl]-N,N-dimethylbenzamide;
(E)-2-[2-[3-[2-[4-(cyclobutyl)-2-thiazolyl]ethenyl]phenylamino]-2-oxoethyl]benzyl alcohol;
(E)-3-[2-[3-[2-[4-(cyclobutyl)-2-thiazolyl]ethenyl]phenylamino]-2-oxoethyl]benzoic acid;
(E)-4-[2-[3-[2-[4-(cyclobutyl)-2-thiazolyl]ethenyl]phenylamino]-2-oxoethyl]benzoic acid;
(E)-2-[2-[3-[2-[4-(cyclopentyl)-2-thiazolyl]ethenyl]phenylamino]-2-oxoethyl]benzoic acid;
(E)-2-[2-[3-[2-[4-(cyclohexyl)-2-thiazolyl]ethenyl]phenylamino]-2-oxoethyl]benzoic acid;
(E)-2-[2-[3-[2-[4-(cycloheptyl)-2-thiazolyl]ethenyl]phenylamino]-2-oxoethyl]benzoic acid;
(E)-2-[2-[3-[2-[4-(cyclooctyl)-2-thiazolyl]ethenyl]phenylamino]-2-oxoethyl]benzoic acid;
(E)-2-[2-[3-[2-[4-(cyclobutyl)-2-thiazolyl]ethenyl]phenylamino]-2-oxoethyl]benzene acetic acid;
(E)-2-[2-[3-[2-[4-(1-methylethyl)-2-thiazolyl]ethenyl]phenylamino]-2-oxoethyl]benzene acetic acid;
(E)-3-[2-[3-[2-[4-(1-methylethyl)-2-thiazolyl]ethenyl]phenylamino]-2-oxoethyl]phenyl acetic acid;
(E)-2-[2-[4-methyl-3-[2-[4-(1-methylethyl)-2-thiazolyl]ethenyl]phenylamino]-2-oxoethyl]benzoic acid;
(E)-2-[2-[4-chloro-3-[2-[4-(1-methylethyl)-2-thiazolyl]ethenyl]phenylamino]-2-oxoethyl]benzoic acid;
(E)-2-[2-[3-[2-[4-(ethoxycarbonyl)-2-thiazolyl]ethenyl]phenylamino]-2-oxoethyl]benzoic acid;
(E)-2-[2-[3-[2-(2-cyclobutyl-4-thiazolyl)ethenyl]phenylamino]-2-oxoethyl]benzoic acid;
(E)-2-[3-[3-[2-[4-(cyclobutyl)-2-thiazolyl]ethenyl]phenylamino]-3-oxopropyl]benzoic acid;
(E)-2-[[[[3-[2-(4-cyclobutyl-2-thiazolyl)ethenyl]phenyl]carbonyl]amino]methyl]benzoic acid;
(E)-5-nitro-2-[2-[3-[2-[4-(cyclobutyl)-2-thiazolyl]ethenyl]phenylamino]-2-oxoethyl]benzoic acid;
(E)-5-chloro-2-[2-[3-[2-[4-(cyclobutyl)-2-thiazolyl]ethenyl]phenylamino]-2-oxoethyl]benzoic acid;
(E)-3-fluoro-2-[2-[3-[2-[4-(cyclobutyl)-2-thiazolyl]ethenyl]phenylamino]-2-oxoethyl]benzoic acid;
(E)-5-methoxy-2-[2-[3-[2-[4-(cyclobutyl)-2-thiazolyl]ethenyl]phenylamino]-2-oxoethyl]benzoic acid;
(E)-5-fluoro-2-[2-[3-[2-[4-(cyclobutyl)-2-thiazolyl]ethenyl]phenylamino]-2-oxoethyl]benzoic acid;
(E)-4-[2-[3-[2-[4-(cyclobutyl)-2-thiazolyl]ethenyl]phenylamino]-2-oxoethyl]-3-methoxy benzoic acid; and
(E)-2-[2-[3-[(2-carboxyphenyl)-1-oxoethyl]amino]phenyl]ethenyl]-4-thiazole carboxylic acid.

Particularly preferred compounds of formula I of the invention are:

(E)-2-[2-[3-[2-[4-(cyclobutyl)-2-thiazolyl]ethenyl]phenylamino]-2-oxoethyl]benzoic acid;
(E)-2-[2-[3-[2-[4-(cyclobutyl)-2-thiazolyl]ethenyl]phenylamino]-2-oxoethyl]benzoic acid methyl ester;
(E)-5-acetoxy-2-[2-[3-[2-[4(cyclobutyl)-2-thiazolyl]ethenyl]phenylamino]-2-oxoethyl]benzoic acid;
(E)-2-[2-[3-[2-[4-(cyclobutyl)-2-thiazolyl]ethenyl]phenylamino]-2-oxoethyl]-N,N-dimethylbenzamide;
(E)-2-[2-[3-[2-[4-(cyclopentyl)-2-thiazolyl]ethenyl]phenylamino]-2-oxoethyl]benzoic acid;
(E)-2-[2-[3-[2-[4-(cyclohexyl)-2-thiazolyl]ethenyl]phenylamino]-2-oxoethyl]benzoic acid;
(E)-2-[2-[3-[2-[4-(1-methylethyl)-2-thiazolyl]ethenyl]phenylamino]-2-oxoethyl]benzoic acid;
(E)-2-[2-[3-[2-[4-(cyclopropyl)-2-thiazolyl]ethenyl]phenylamino]-2-oxoethyl]benzoic acid;
(E)-2-[2-[3-[2-[4-(cyclobutyl)-2-thiazolyl]ethenyl]phenylamino]-2-oxoethyl]benzyl alcohol;
(E)-5-chloro-2-[2-[3-[2-[4-(cyclobutyl)-2-thiazolyl]ethenyl]phenylamino]-2-oxoethyl]benzoic acid;
(E)-5-methoxy-2-[2-[3-[2-[4-(cyclobutyl)-2-thiazolyl]ethenyl]phenylamino]-2-oxoethyl]benzoic acid; and
(E)-2-[[[[3-[2-(4-cyclobutyl-2-thiazolyl)ethenyl]phenyl]carbonyl]amino]methyl]benzoic acid.

The compounds of formula I can be prepared as hereinafter described in Reaction Schemes I-XI.

Scheme I

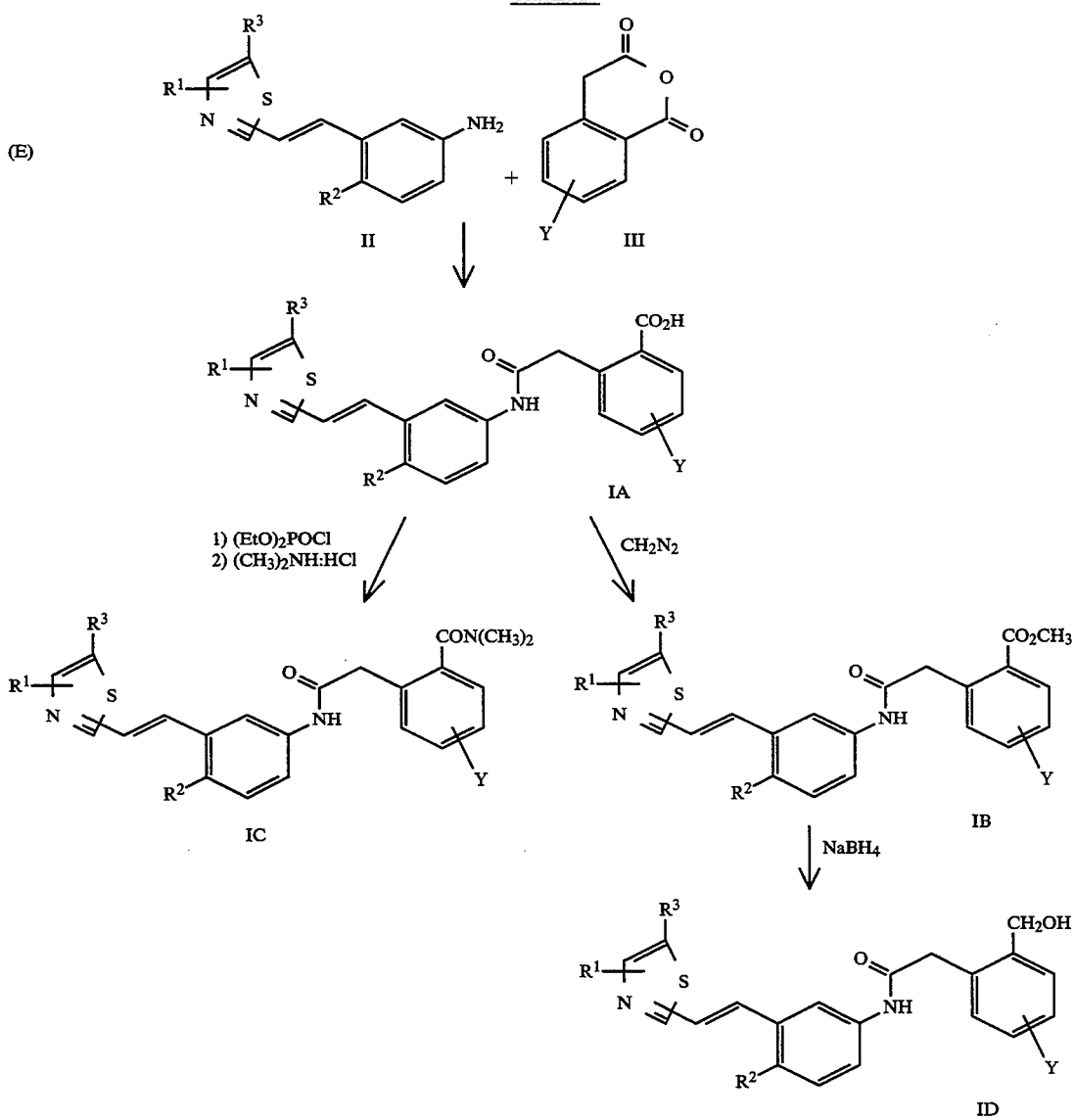

wherein $R^1$, $R^2$, $R^3$ and Y are as previously described.

In Reaction Scheme I, a compound of formula II, which are known compounds, or can be made by known methods, is reacted with a compound of formula III, known compounds or which can be made by known methods, to form a corresponding compound of formula IA, at a temperature in the range of from about 25° C. to about 150° C. in the presence of an inert solvent, preferably toluene, preferably at 100° C. The resulting compound of formula IA can be recovered utilizing known procedures, for example, crystallization, chromatography and the like.

Alternatively, a compound of formula IA can be treated with diazomethane and converted to the corresponding compound of formula IB in the presence of an inert solvent, for example, diethylether or diethylether mixed with other inert solvents such as methylene chloride or methanol or the like, at a temperature in the range of from about 0° C. to about 25° C. A resulting compound of formula IB can be recovered utilizing known procedures, for example, crystallization, and chromatography and the like.

The compound of formula IA can alternatively be converted to the corresponding compound of formula IC by reacting with diethylchlorophosphate, dimethylamine hydrochloride and triethylamine in the presence of an ether solvent, for example, tetrahydrofuran or the like, at a temperature in the range of from about 0° C. to about 50° C., preferably at 25° C., under an inert atmosphere. A resulting compound of formula IC can be recovered utilizing known procedures, for example, crystallization, and the like.

The compound of formula IB can be converted to the corresponding compound of formula ID by reacting with a reducing agent such as, preferably, sodium borohydride in the presence of an inert solvent such as tetrahydrofuran or methanol or a combination thereof at a temperature in the range of from about 0° C. to about 50° C., preferably 25° C. A resulting compound of formula ID can be recovered by known procedures, for example, chromatography, and the like.

Scheme II

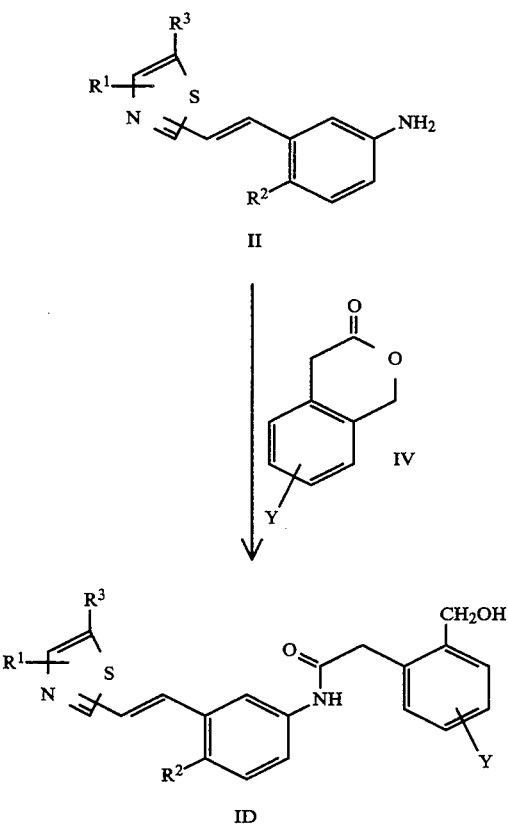

wherein $R^1$, $R^2$, $R^3$ and Y are as previously described.

In Reaction Scheme II, a compound of formula II is converted to a corresponding compound of formula ID by reacting with a compound of formula IV, known compounds or which can be made utilizing known methods, at a temperature in the range of from about 100° C. to about 150° C. A resulting compound of formula ID can be recovered utilizing known procedures, for example, chromatography, and the like.

Scheme III

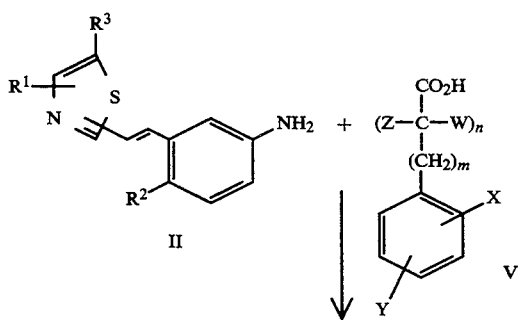

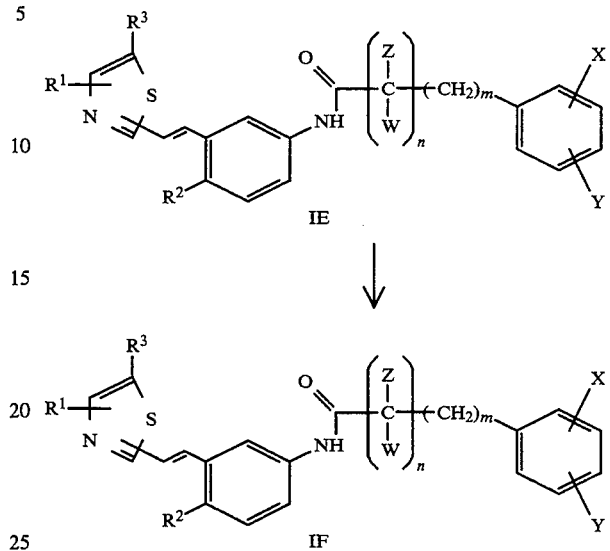

wherein X is —$COR^5$ or —$R^4COR^5$ with the proviso that $R^5$ is not hydroxy in the compounds of formulas V and IE; $R^1$, $R^2$, $R^5$, $R^3$, m, n, W, Z, and Y are as previously described.

In Reaction Scheme III, a compound of formula II is converted to a corresponding compound of formula IE by reacting with a compound of formula V, known compounds or which can be made by known methods, in the presence of a condensing agent, for example, a carbodiimide such as N-ethyl-N-(dimethylaminopropyl) carbodiimide, and the like, at a temperature in the range of from about 0° C. to about 25° C. A resulting compound of formula IE can be recovered utilizing known procedures for example, crystallization and the like.

The compound of formula IE is converted to a corresponding compound of formula IF by reacting with a base, such as sodium hydroxide or lithium hydroxide monohydrate in the presence of an inert solvent, for example, tetrahydrofuran or methanol admixed with water at a temperature in the range of from about 0° C. to about 100° C., preferably at about 25° C. A resulting compound of formula IF can be recovered after neutralization with acid, such as dilute hydrochloric acid or glacial acetic acid, utilizing known procedures for example, crystallization, and the like.

Scheme IV

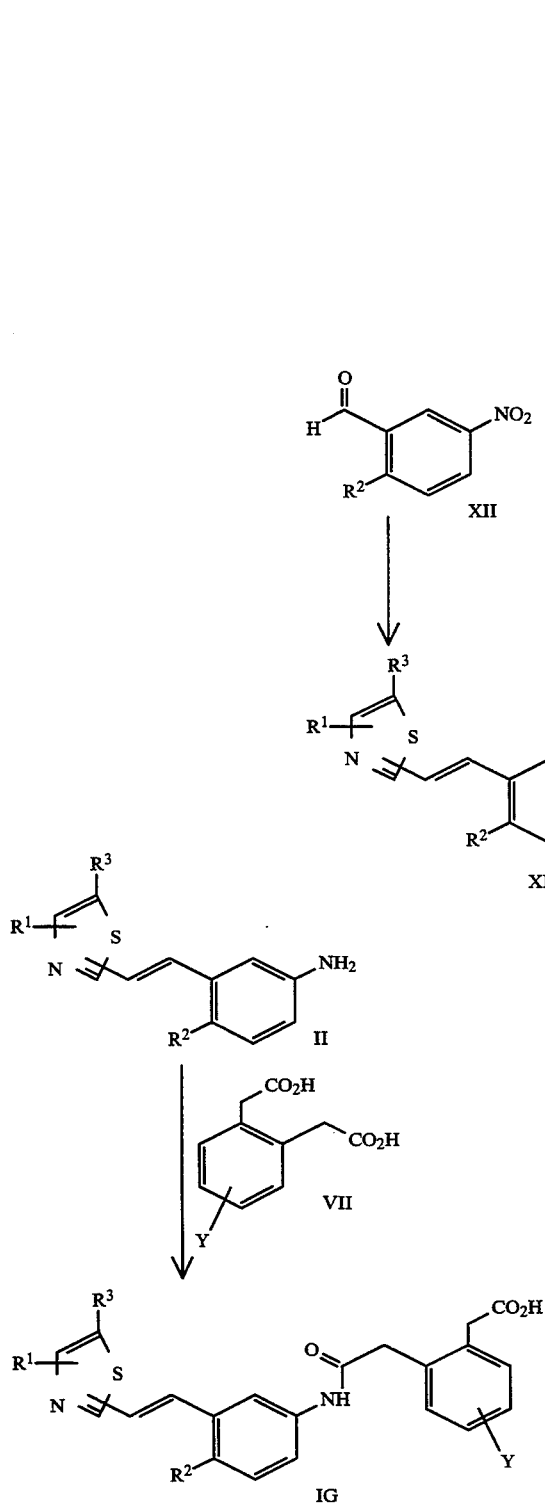

wherein $R^1$, $R^2$, $R^3$ and Y are as previously described.

In Reaction Scheme IV, a compound of formula II is convened to a corresponding compound of formula IG by reacting with a compound of formula VII, known compounds or which can be made by known methods, in the presence of a condensing agent, for example, a carbodiimide such as N-ethyl-N-(dimethylaminopropyl) carbodiimide, and the like, at a temperature in the range of from about 0° C. to about 25° C. A resulting compound of formula IG can be recovered utilizing known procedures, for example, crystallization and the like.

Scheme V

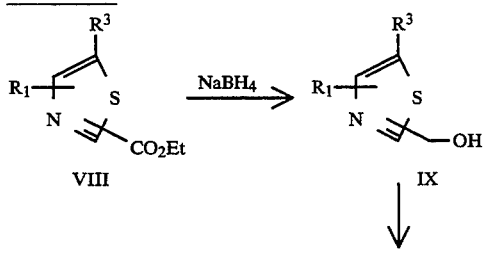

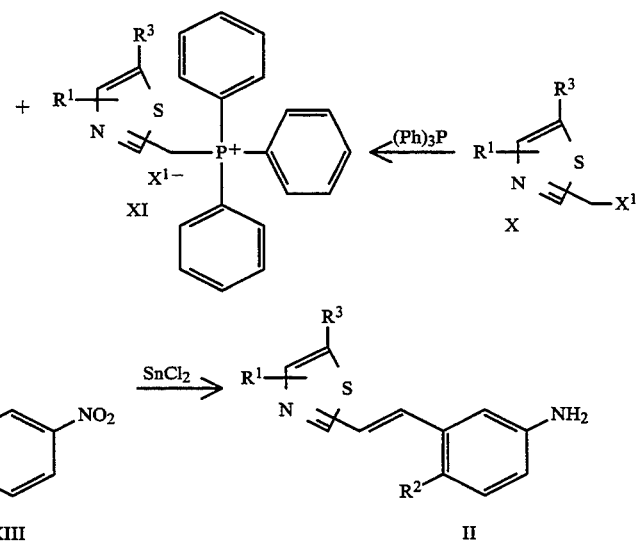

wherein $X^1$ is halogen other than fluorine and $R^1$, $R^2$ and $R^3$ are as described above.

In Reaction Scheme V, a compound of formula VIII, which can be prepared by the process of Reaction Schemes VIII and IX, is converted to a corresponding compound of formula IX, by reacting with a reducing agent such as $NaBH_4$ or $LiBH_4$ in the presence of an alcohol or ether solvent, at a temperature in the range of from 0° C. to 50° C., preferably at 25° C.

The compound of formula IX can be converted to a corresponding compound of formula X by reacting with a halogenating agent, such as, thionyl chloride or triphenylphosphonium-bromide in the presence of an inert solvent such as, methylene chloride or an aromatic hydrocarbon such as, toluene at a temperature in the range of from 0° C. to 50° C., preferably 25° C.

The compound of formula X can be converted to a corresponding compound of formula XI by reaction with triphenylphosphine in an inert solvent, such as toluene, or acetonitrile, at a temperature range of 25° C. to 180° C., preferably 80° C.

The compound of formula XI is reacted with a strong base such as butyllithium or sodium hydride and then reacted with a compound of formula XII, known compounds or which can be made by known methods, to form a corresponding compound of formula XIII, in an ether solvent, for example, tetrahydrofuran at a temperature in the range of from about 0° C. to about 50° C., preferably at about 25° C.

Thereafter, a compound of formula XIII is reduced to the corresponding compound of formula II by utilizing a reducing agent, for example, stannous chloride, in the presence of an inert solvent, for example, an alkanol, such as ethanol, at a temperature in the range of from about 0° C. to about 100° C. The resulting compound of formula II can be recovered by utilizing known procedures, for example, extraction, chromatography and the like.

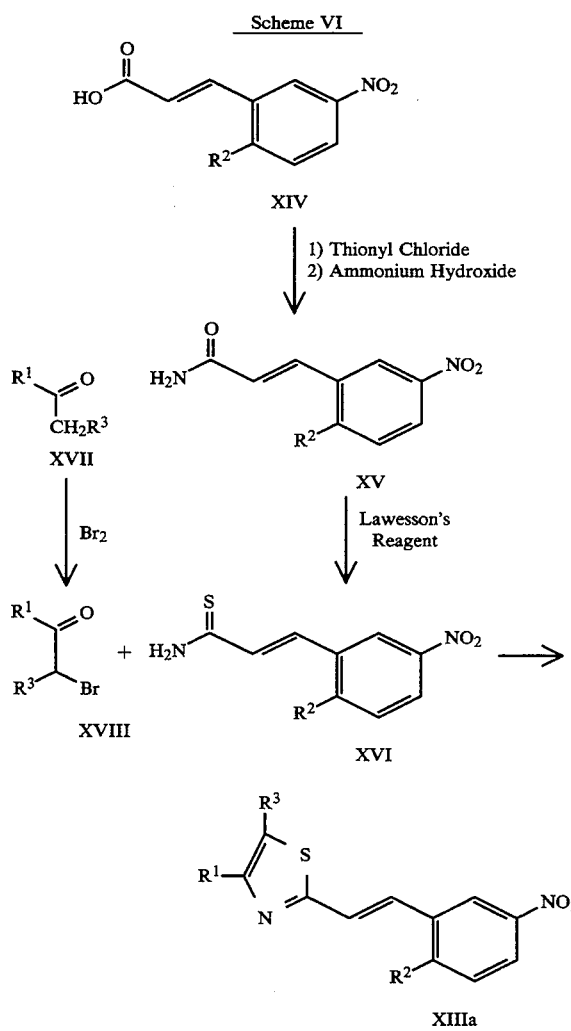

wherein $R^1$, $R^2$, and $R^3$ are as previously described.

In Reaction Scheme VI, a compound of formula XVII, which are known compounds or can be prepared according to known procedures is halogenated to the corresponding compound of formula XVIII in the presence of an alkanol, for example, methanol, and a halogenating agent, for example, bromine at a temperature in the range of from about 10° C. to about room temperature. The resulting compound of formula XVIII can be recovered utilizing known procedures, for example, distillation, chromatography and the like or can be used in the preparation of a compound of formula XIIIa, as set forth below, without purification.

The compound of formula XIV, which are known compounds or can be prepared by known methods, is converted to a corresponding compound of formula XV by treatment with a chlorinating agent, such as, oxalyl chloride, thionyl chloride, $PCl_3$ and the like, at a temperature of 25° C.-100° C., preferably 60° C. followed by reaction with ammonium hydroxide.

A compound of formula XV is converted to a corresponding compound of formula XVI by treatment with a thiolating agent, for example, phosphorous pentasulfide or Lawesson's reagent in the presence of an inert solvent, such as tetrahydrofuran or the like, at a temperature of 0° C.-50° C., preferably 25° C. The resulting compound of formula XVI can be recovered utilizing known procedures, for example, crystallization, chromatography and the like.

Thereafter, a compound of formula XVIII is reacted with a compound of formula XVI conveniently in the presence of an inert solvent, for example, an alkanol, such as, ethanol, or the like at a temperature in the range of from about 0° C. to about 100° C. A resulting compound of formula XIIIa can be recovered utilizing known procedures, for example, crystallization, chromatography and the like.

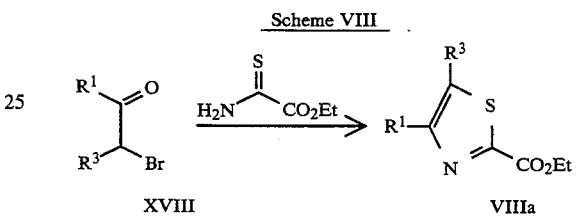

wherein $R^1$ and $R^3$ are as previously described.

In Reaction Scheme VIII a compound of formula XVIII, is reacted with ethyl thiooxamate to form a compound of formula VIIIa in the presence of an alcohol solvent, at preferably the reflux temperature of the reaction mixture.

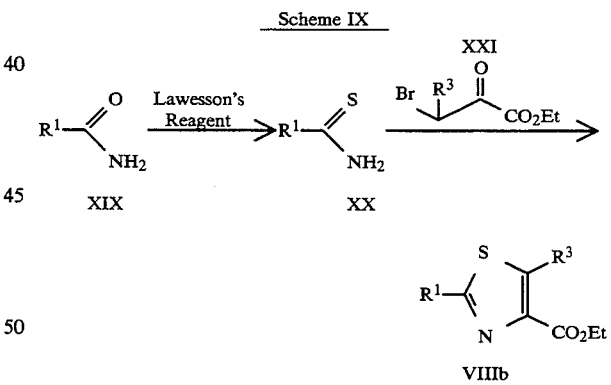

wherein $R^1$ and $R^3$ are as previously described.

In Reaction Scheme IX, a compound of formula XIX, known compounds or which can be prepared by known methods, is converted to a corresponding compound of formula XX by treatment with a thiolating agent, for example, Lawesson's Reagent in the presence of an inert solvent, for example, an ether, such as, tetrahydrofuran or the like, at room temperature.

A compound of formula XX is converted to a corresponding compound of formula VIIIb by reacting with a compound of formula XXI, known compounds or which can be prepared by known methods, in the presence of an alcohol solvent at a temperature in the range of from 0° C. to about 100° C., preferably 80° C. The resulting compound of formula VIIIb can be recovered utilizing known procedures, such as, for example, crystallization and the like.

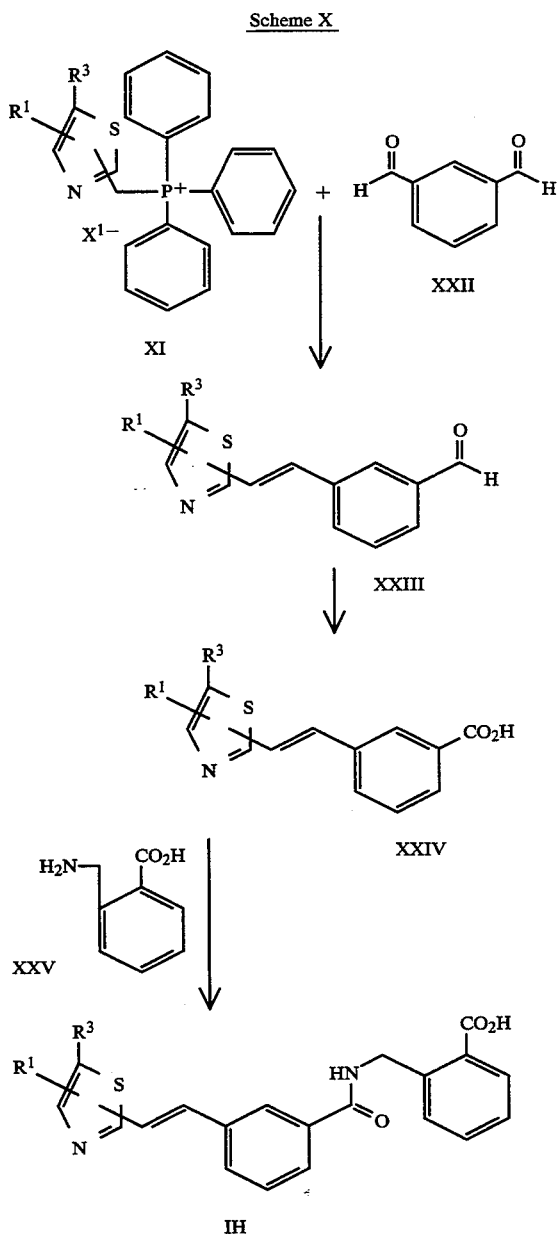

Scheme X wherein $R^1$, $R^3$ and $X^1-$ are as previously described.

In Reaction Scheme X, a compound of formula XI, prepared in accordance with Scheme V, is converted to a corresponding compound of formula XXIII by reacting with a compound of formula XXII, a known compound, in the presence of an inert solvent, such as, for example, tetrahydrofuran and the like, at a temperature in the range of from about 0° C. to about 50° C. under an inert atmosphere such as argon. A resulting compound of formula XXIII can be recovered by known procedures, for example, chromatography and the like.

A compound of formula XXIII can be converted to a corresponding compound of formula XXIV by air oxidizing under basic conditions and normal atmospheric conditions.

A compound of formula XXIV is converted to a corresponding compound of formula IH, by reacting with a compound of formula XXV, a known compound, and a chlorinating agent, such as, for example, thionyl chloride or oxalyl chloride. A resulting compound of formula IH can be recovered utilizing known procedures, such as, for example, chromatography and the like.

This invention also relates to the salts of the compounds of formula I, their enantiomers, diastereomers and racemates, which salts can be prepared by the reaction of the said compounds with a base having a non-toxic, pharmaceutically acceptable cation. In general, any base which will form a salt with a carboxylic acid and whose pharmacological properties will not cause an adverse physiological effect when ingested is considered as being within the scope of this invention. Suitable bases thus include, for example, the alkali metal and alkaline earth metal hydroxides and carbonates, ammonia, primary, secondary and tertiary amines, such as, monoalkylamines, dialkylamines, trialkylamines, nitrogen containing heterocyclic amines, for example, piperidine and the like.

The compounds of formula I of the invention, when $R^1$, $R^2$ and $R^3$ are alkyl, n is 1 and Z and W are different alkyl, possess one or two asymmetric carbon atoms, they can thus be obtained as enantiomers, diastereomeric or as racemic mixtures. The enantiomers can be obtained by utilizing optically active starting materials which are commercially available or can be prepared according to known methods. Alternatively, the enantiomeric mixtures can be separated by conventional methods. The resolution of racemates into the optically active isomers can be carried out by known procedures. Some racemic mixtures can be precipitated as eutectics and can thereafter be separated. Chemical resolution is, however, preferred. By this method, diastereomeric salts are formed from the reacemic mixture of a compound of formula I, with an optically active resolving agent, for example, an optically active base, such as R-(+)-α-methylbenzylamine. The formed diastereomers are separated by fractional crystallization and converted to the corresponding optical isomer by treatment with acid. Thus, the invention covers the racemates of the compounds of formula I as well as their optically active isomers (enantiomers).

The compounds of formula I and their pharmaceutically acceptable salts are active as inhibitors of bronchoconstriction and are therefor useful as bronchopulmonary agents, for example, in the relief of asthma and allergic reactions. The useful activity of the compounds of formula I of the invention can be demonstrated as hereinafter set forth.

LTD$_1$ RECEPTOR LIGAND BINDING ASSAY

Method

A lung homogenate was prepared from guinea pig lung membranes and was resuspended in buffer containing 10 mM Tris·HCl (pH 7.5) (Hogaboom et al., Complete cite 1983). Optimum assay conditions were determined with an assay mixture containing: 10 mM Tris·HCl (pH 7.5); 0.1% bovine serum albumin (BSA); 1 mM glycine; 1 mM cysteine; 3.5 nM [$^3$H]LTD$_4$ and the membrane preparation (100–200 g protein) in a final volume of 250 ml. The incubation was carried out at 20° C. for 30 minutes. At 20° C., binding increased linearly with protein concentration, reached equilibrium in 20 minutes, was saturable, and was reversible upon addition of 1 mM unlabelled LTD$_4$. Separation of bound from free [$^3$H]LTD$_4$ as performed by rapid filtration on GF/C glass fiber filters (Whatman International Ltd., Maidstone, England) and washing with two 4-ml aliquots of Tyrode solution (0.9 g/100 ml NaCl; 0.02 g/100 ml KCl; 0.02 g/100 ml CaCl$_2$; 0.01 g/100 ml MgCl$_2$; 0.1 g/100 ml glucose; 0.1 g/100 ml NaHCO$_3$; 0.005 g/100 ml NaH$_2$PO$_4$)containing 0.1% BSA. Radioactivity remaining on the filters was measured in 10 ml of Aquasol. Specific binding, was defined as that displaced by 1 mM unlabelled LTD$_4$, and was 95% of total binding.

The inhibition of [$^3$H]LTD$_4$ specific binding by an antagonist is related to the LTD$_4$ content of that sample by regression analysis from a "standard curve" of the inhibition of [$^3$H]LTD$_4$ specific binding by nonlabeled LTD$_4$. The median inhibitory concentration (IC$_{50}$ value) was determined by linear regression of log concentration-response curves generated by at least 3 concentrations that caused statistically significant inhibition between 10 and 90%. Results are expressed as mean±S. E. M. (standard error of the mean) of n independent experiments (separate receptor batches) conducted in duplicates.

TABLE I
RESULTS

| Compound | LTD$_4$ Binding IC$_{50}$ ($\mu$M) |
| --- | --- |
| (E)-2-[2-[3-[2-[4-(1-methylethyl)-2-thiazolyl]ethenyl] phenylamino]-2-oxoethyl]benzoic acid | 0.004 |
| (E)-2-[2-[3-[2-[4-(cyclopropyl)-2-thiazolyl]ethenyl] phenylamino]-2-oxoethyl]benzoic acid | 0.003 |
| (E)-2-[2-[3-[2-[4-(cyclobutyl)-2-thiazolyl]ethenyl] phenylamino]-2-oxoethyl]benzoic acid | 0.003 |
| (E)-2-[2-[3-[2-[4-(cyclobutyl)-2-thiazolyl]ethenyl] phenylamino]-2-oxoethyl]benzeneacetic acid | 1.0 |
| (E)-2-[2-[3-[2-[4-(1-methylethyl)-2-thiazolyl]ethenyl] phenylamino]-2-oxoethyl]benzene acetic acid | 1.0 |
| (E)-3-[3-[2-[4-(1-methylethyl)-2-thiazolyl]ethenyl] phenylamino]-2-oxoethylphenylacetic acid | 1.0 |
| (E)-2-[2-[4-chloro-3-[2-[4-(1-methylethyl)-2-thiazolyl] ethenyl]phenylamino]-2-oxoethyl]benzoic acid | 0.9 |

Antagonism of Bronchoconstriction in Guinea Pigs

Male guinea pigs (Hartley strain, Charles River) weighing 400-600 g were anesthetized with urethane (2 g/kg) intraperitoneally, and a polyethylene cannula was inserted into the jugular vein for intravenous drug administration. Tracheal pressure (cm of H$_2$O) was recorded from a Statham pressure transducer (P 32 AA). Propranolol was administered 5 minutes prior to challenge with LTD$_4$. Two minutes later spontaneous breathing was arrested with succinylcholine chloride (1.2 mg/kg) administered intravenously, and the animals were ventilated with a Harvard (Model 680) small animal respirator set at 40 breaths/min and a 4.0 cc stroke volume. Control vehicle (DMSO) or test compound was administered through the cannula into the jugular vein 1 minute before the animals were challenged with a maximum constrictory dose of LTD$_4$ (25 mg/kg I.V.) given intravenously. The change in tracheal pressure was averaged for control and drug-treated animals and percent inhibition was calculated. For determination of oral activity, animals were dosed with test compound or vehicle (PEG400) two hours prior to challenge with LTD$_4$ (25 mg/kg, i.v.).

The relative potency of test compounds administered by the intravenous and oral route was determined by administering increasing doses of test compound at a fixed pretreatment time. The median inhibitory dose (ID$_{50}$ value) was determined by linear regression of log dose-response curves generated by at least 3 doses that caused statistically significant inhibition between 10 and 90%. The correlation coefficient for the regression line was always greater than 0.95. For determination of the time-course of inhibition for various compounds, the time between administration of compound and challenge with LTD$_4$ was varied. Durations of action were defined as the time for inhibitory activity to decrease to 50%.

TABLE II
RESULTS
LTD$_4$ - INDUCED BRONCHOCONSTRICTION

| Compound Example No. | ID$_{50}$ mg/kg, I.V. | ID$_{50}$ mg/kg p.o. |
| --- | --- | --- |
| 1 | 0.008 | 0.5 |
| 2 | 0.01 | 0.22 |
| 3 | 0.01 | 0.22 |
| 4 | 0.3 | 0.3 |
| 5 | 0.005 | 0.6 |
| 6 | 0.1 | 0.3 |
| 7b | 0.3 | ND |
| 8b | 50 ± 6%* | ND |
| 9 | 0.005 | 0.40 |
| 10 | 0.02 | 0.43 |
| 11i | 0.02 | 42 ± 10%* |
| 12d | 0.15 | 24 ± 4%* |
| 13 | 0.01 | 0.78 |
| 14 | 0.05 | 41 ± 8%* |
| 15 | 40 ± 7%* | ND |
| 16g | 0.2 | 24 ± 8%* |
| 17e | 0.28 | 26 ± 7%* |
| 18c | 0.2 | 13 ± 3%* |
| 19 | 12 ± 4%*** | ND |
| 20h | 0.04 | 48 ± 6%* |
| 21b | 0.02 | 8.2 |
| 22c | 0.04 | 0.1 |
| 23 | 36 ± 6%* | ND |
| 24 | 0.01 | 0.2 |
| 25 | 0.03 | 36 ± 6%* |
| 26 | 0.03 | 0.2 |
| 27 | 0.2 | ND |
| 28b | 0.4 | ND |
| 31 | 0.004 | 0.3 |

*ID$_{50}$ value not determined, value reported is percent inhibition at 1 mg/kg
ND = not determined
**A previous test resulted in 0 ± 0% inhibition at 1 mg/kg A compound of formula I, an enantiomer, a diastereomer or racemate thereof or a salt thereof or a composition containing a therapeutically effective amount of a compound of formula I, an enantiomer, a diastereomer or racemate thereof or a salt thereof can be administered by methods well known in the art. Thus, a compound of formula I, an enantiomer, a diastereomer or racemate thereof or a salt thereof can be administered either singly or with other pharmaceutical agents, for example, antihistamines, mediator release inhibitors, methyl xanthines, beta agonists or antiasthmatic steroids such as prednisone and prednisoline, orally, parenterally, rectally, or by inhalation, for example, in the form of an aerosol, micropulverized powder or nebulized solution. For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered in solutions or suspension, for example, as an aqueous or peanut oil solution or suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in a pressurized container fitted with an aerosol valve suitable for release of the pressurized compositions. Preferably, the aerosol valve is a metered valve, that is one which on activation releases a predetermined effective dose of the aerosol composition.

In the practice of the invention, the dose of a compound of formula I or a salt thereof to be administered and the frequency of administration will be dependent on the potency and duration of activity of the particular compound of formula I or salt to be administered and on the route of administration, as well as the severity of the condition, age of the mammal to be treated and the like. Oral doses of a compound of formula I or a salt thereof contemplated for use in practicing the invention are in the range of from about 1 mg to about 1000 mg per day, preferably about 1 to about 250 mg either as a single dose or in divided doses.

The examples which follow further illustrate the invention. All temperatures are in degrees celsius unless otherwise stated.

EXAMPLE 1

(E)-2-[2-[3-[2-[4-(1-Methylethyl)-2-thiazolyl]ethenyl]-phenylamino]-2-oxoethyl]benzoic acid A mixture of 1.2 g of (E)-3-[2-[4-(1-methylethyl)-2-thiazolyl]ethenyl]benzeneamine, 0.8 g of homophthalic anhydride and 25 ml of toluene was heated to reflux for 0.5 hr. Upon cooling to room temperature, the solid reaction product was filtered and washed with ethyl ether to yield 1.7 g of (E)-2-[2-[3-[2-[4-(1-methylethyl)-2-thiazolyl]ethenyl]phenylamino]-2-oxoethyl]benzoic acid. Recrystallization from ethyl alcohol yielded off-white solid material; m.p. 203°–204° C.

Anal. Calcd for $C_{23}H_{22}N_2O_3S$: C, 67.96; H, 5.46; N, 6.89. Found: C, 67.77; H, 5.36; N, 6.71.

EXAMPLE 2

(E)-2-[2-[3-[2-[4-(Cyclopropyl)-2-thiazolyl]ethenyl]-phenylamino]-2-oxoethyl]benzoic acid A solution of 5.0 g of (E)-3-[2-[4-(cyclopropyl)-2-thiazolyl]ethenyl]benzeneamine, 3.35 g of homophthalic anhydride, and 100 ml of toluene was heated to reflux for 0.5 hr. After cooling, the solids that formed were collected by filtration and this material was triturated with ethyl ether to yield 7.4 g of (E)-2-[2-[3-[2-[4-(cyclopropyl)-2-thiazolyl]ethenyl]phenylamino]-2-oxoethyl]benzoic acid. Recrystallization from acetonitrile yielded 5.1 g of material; m.p. 200°–201° C.

Anal. Calcd for $C_{23}H_{20}N_2O_3S$: C, 68.30; H, 4.98; N, 6.93. Found: C, 67.92; H, 4.97; N, 6.83.

EXAMPLE 3

(E)-2-[2-[3-[2-[4-(Cyclobutyl)-2-thiazolyl]ethenyl]-phenylamino]-2-oxoethyl]benzoic acid A solution of 1.28 g of (E)-3-[2-[4-(cyclobutyl)-2-thiazolyl]ethenyl]benzeneamine, 0.81 g of homophthalic anhydride, 50 ml of toluene and 25 ml of tetrahydrofuran was heated to reflux for 0.5 hr. The solvents were removed by rotary evaporation and the residual materials were triturated with ethyl ether to yield 1.15 g of (E)-2-[2-[3-[2-[4-(cyclobutyl)-2-thiazolyl]ethenyl]-phenylamino]-2-oxoethyl]benzoic acid. Recrystallization from acetonitrile yielded 0.81 g of material; m.p. 204°–206° C.

Anal. Calcd for $C_{24}H_{22}N_2O_3S$: C, 68.88; H, 5.30; N, 6.69. Found: C, 68.15; H, 5.21; N, 6.54.

EXAMPLE 4

(E)-2-[2-[3-[2-[4-(Cyclobutyl)-2-thiazolyl]ethenyl]-phenylamino]-2-oxoethyl]benzoic Acid Methyl Ester A suspension of 2.1 g of (E)-2-[2-[3-[2-[4-(cyclobutyl)-2-thiazolyl]ethenyl]phenylamino]-2-oxoethyl]benzoic acid in 200 ml of ethyl ether/methylene chloride (1:3 v/v) was treated with an excess of an ethyl ether solution of diazomethane. After 10 min the excess of diazomethane was removed with a stream of nitrogen, the remaining solvents were removed in vacuo and the residual materials were taken up into methylene chloride. This solution was washed with water (2×15 ml) and dried (MgSO₄). Removal of the volatiles in vacuo and recrystallization from ethyl acetate yielded 2.2 g of (E)-2-[2-[3-[2-[4-(cyclobutyl)-2-thiazolyl]ethenyl]phenylamino]-2-oxoethyl]benzoic acid methyl ester as an off-white solid, m.p. 143°–144° C.

Anal. Calcd for $C_{25}H_{24}N_2O_3S$: C, 69.42; H, 5.59; N, 6.48. Found: C, 69.21; H, 5.63; N, 6.49.

EXAMPLE 5

(E)-2-[2-[3-[2-[4-(Cyclobutyl)-2-thiazolyl]ethenyl]-phenylamino]-2-oxoethyl]-N,N-dimethylbenzamide A mixture of 0.836 g of (E)-2-[2-[3-[2-[4-(cyclobutyl)-2-thiazolyl]ethenyl]phenylamino]-2-oxoethyl]benzoic acid, 0.38 g of diethylchlorophosphate, 2.2 g of triethylamine, 1.8 g of dimethylamine hydrochloride and 25 ml of tetrahydrofuran was stored at room temperature for 20 hr. The solvent was removed in vacuo and the residual materials were taken up in 100 ml of methylene chloride and then washed with water (3×30 ml), dried (MgSO₄) and the solvent removed in vacuo. The residual materials were crystallized from ethanol to yield (E)-2-[2-[3-[2-[4-(cyclobutyl)-2-thiazolyl]ethenyl]-phenylamino]-2-oxoethyl]-N,N-dimethylbenzamide as an off-white colored solid, m.p. 125°–127° C.

Anal. Calcd for $C_{26}H_{27}N_3O_2S$: C, 70.09; H, 6.11; N, 9.43. Found: C, 69.92; H, 6.25; N, 9.42.

EXAMPLE 6a (E)-2-[2-[3-[2-[4-(Cyclobutyl)-2-thiazolyl]ethenyl]-phenylamino]-2-oxoethyl]benzyl Alcohol A mixture of 0.865 g of (E)-2-[2-[3-[2-[4-(cyclobutyl)-2-thiazolyl]ethenyl]phenylamino]-2-oxoethyl]benzoic acid methyl ester, 0.5 g of sodium borohydride, 75 ml of tetrahydrofuran and 20 ml of methanol was stirred under a positive nitrogen atmosphere for 20 hr. The reaction mixture was condensed in vacuo and the residual materials were mixed with water and extracted with methylene chloride. The combined extracts were washed with water, dried (MgSO₄) and condensed in vacuo. The residual materials were further purified by chromatography over florisil using ethyl acetate as the eluant to yield (E)-2-[2-[3-[2-[4-(cyclobutyl)-2-thiazolyl]ethenyl]phenylamino]-2-oxoethyl]benzyl alcohol.

EXAMPLE 6b (E)-2-[2-[3-[2-[4-(Cyclobutyl)-2-thiazolyl]ethenyl]-phenylamino]-2-oxoethy]benzyl Alcohol A solution of 0.256 g of (E)-3-[2-[4-(cyclobutyl)-2-thiazolyl]ethenyl]benzeneamine and 0.148 g of 3-isochromanone was heated in a 126° C. oil bath for 17 hr. The residual materials were purified by silica gel chromatography using ethyl acetate-hexane (1:4 v/v) as the eluant to yield (E)-2-[2-[3-[2-[4-(cyclobutyl)-2-thiazolyl]ethenyl]phenylamino]-2-oxoethyl]benzyl alcohol.

EXAMPLE 7a (E)-3-[2-[3-[2-[4-(Cyclobutyl)-2-thiazolyl]ethenyl]-phenylamino]-2-oxoethyl]benzoic Acid Methyl Ester A solution composed of 1.0 g of 3-carboxymethyl benzoic acid methyl ester, 1.3 g of (E)-3-[2-[4-(cyclobutyl)-2-thiazolyl]ethenyl]benzeneamine, 1.0 g of N-ethyl-N-(dimethylaminopropyl) carbodiimide, 2.4 g of 4-dimethylaminopyridine and 75 ml of methylene chloride was stored at 0° C. After 16 hr., the reaction mixture was washed with 75 ml of water, dried (MgSO$_4$) and the solvents removed by rotary, evaporation. The residual materials were triturated with ethyl acetate/hexane to yield 1.7 g of (E)-3-[2-[3-[2-[4-(cyclobutyl)-2-thiazolyl]ethenyl]phenylamino]-2-oxoethyl]benzoic acid methyl ester; m.p. 119°-120° C.

EXAMPLE 7b (E)-3-[2-[3-[2-[4-(Cyclobutyl)-2-thiazolyl]ethenyl]-phenylamino]-2-oxoethyl]benzoic acid A solution composed of 0.5 g of (E)-3-[2-[3-[2-[4-(cyclobutyl)-2-thiazolyl]ethenyl]phenylamino]-2-oxoethyl]benzoic acid methyl ester, 20 ml of tetrahydrofuran, 3 ml of methanol, 3 ml of water and 353 mg of lithium hydroxide monohydrate was allowed to stand at room temperature for 20 hr. The solvents were removed by rotary evaporation and the residual materials were taken up in 30 ml of water. Addition of excess acetic acid caused the precipitation of 0.49 g of (E)-3-[2-[3-[2-[4-(cyclobutyl)-2-thiazolyl]ethenyl]phenylamino]-2-oxoethyl]benzoic acid; m.p. 208°-209° C. after recrystallization from 2-propanol.

Anal. Calcd for C$_{24}$H$_{22}$N$_2$O$_3$S: C, 68.88; H, 5.30; N, 6.69. S, 7.66. Found: C, 68.78; H, 5.35; N, 6.55; S, 7.55.

EXAMPLE 8a (E)-4-[2-[3-[2-[4-(Cyclobutyl)-2-thiazolyl]ethenyl]-phenylamino]-2-oxoethyl]benzoic Acid Methyl Ester A solution composed of 1.0 g of 4-carboxymethyl benzoic acid methyl ester, 1.3 g of (E)-3-[2-[4-(cyclobutyl)-2-thiazolyl]ethenyl]benzeneamine, 1.0 g of N-ethyl-N-(dimethylaminopropyl) carbodiimide, 2.4 g of 4-dimethylaminopyridine and 75 ml of methylene chloride at 0° C. After 16 hr. the reaction mixture was washed with 75 ml of water, dried (MgSO$_4$) and the solvents removed by rotary evaporation. The residual materials were recrystallized with ethyl acetate to yield 2.1 g of (E)-4-[2-[3-[2-[4-(cyclobutyl)-2-thiazolyl]ethenyl]phenylamino]-2-oxoethyl]benzoic acid methyl ester; m.p. 163°-164° C.

EXAMPLE 8b (E)-4-[2-[3-[2-[4-(Cyclobutyl)-2-thiazolyl]ethenyl]-phenylamino]-2-oxoethyl]benzoic acid A solution composed of 0.5 g of (E)-4-[2-[3-[2-[4-(cyclobutyl)-2-thiazolyl]ethenyl]phenylamino]-2-oxoethyl]benzoic acid methyl ester, 20 ml of tetrahydropyran, 3 ml of methanol, 3 ml of water and 0.35 g of lithium hydroxide monohydrate was allowed to stand at room temperature for 20 hr. The solvents were removed by rotary evaporation and the residual materials were taken up in 30 ml of water. Addition of an excess of acetic acid caused the precipitation of 0.5 g of (E)-4-[2-[3-[2-[4-(cyclobutyl)-2-thiazolyl]ethenyl]-phenylamino]-2-oxoethyl]benzoic acid; m.p. 262°-263° C. after recrystallization from 2-propanol.

Anal. Calcd for C$_{24}$H$_{22}$N$_2$O$_3$S: C, 68.88; H, 5.30; N, 6.69; S, 7.66. Found: C 68.60; H, 5.30; N, 6.61; S, 7.59.

EXAMPLE 9

(E)-2-[2-[3-[2-[4-(Cyclopentyl)-2-thiazolyl]ethenyl]-phenylamino]-2-oxoethyl]benzoic acid A solution of 2.7 g of (E)-3-[2-[4-(cyclopentyl)-2-thiazolyl]ethenyl]benzeneamine, 1.78 g of homophthalic anhydride and 40 ml of toluene was heated to reflux for 0.5 hr. Cooling and filtration yielded 3.75 g of (E)-2-[2-[3-[2-[4-(cyclopentyl)-2-thiazolyl]ethenyl]-phenyl=amino]-2-oxoethyl]benzoic acid; m.p. 209°-210° C. from tetrahydrofuran.

Anal. Calcd for C$_{25}$H$_{24}$N$_2$O$_3$S: C, 69.42; H, 5.59; N, 6.48. Found: C, 69.56; H, 5.48; N, 6.56.

EXAMPLE 10

(E)-2-[2-[3-[2-[4-(Cyclohexyl)-2-thiazolyl]ethenyl]-phenylamino]-2-oxoethyl]benzoic acid A solution of 2.8 g of (E)-3-[2-[4-(cyclohexyl)-2-thiazolyl]ethenyl]benzeneamine, 1.78 g of homophthalic anhydride and 30 ml of toluene were heated to reflux for 0.5 hr. Cooling and filtration yielded 4.12 g of (E)-2-[2-[3-[2-[4-(cyclohexyl)-2-thiazolyl]ethenyl]-phenylamino]-2-oxoethyl]benzoic acid; m.p. 210°-211° C. from tetrahydrofuran.

Anal. Calcd for C$_{26}$H$_{26}$N$_2$O$_3$S: C, 69.63; H, 5.87; N, 6.27. Found: C, 69.94; H, 5.93; N, 6.29.

EXAMPLE 11a

Bromomethyl Cycloheptyl Ketone

An ice cold solution of 19.0 g of cycloheptyl methyl ketone in 100 ml of methyl alcohol was treated dropwise with 7 ml of bromine. After 5 min, the ice bath was removed and the reaction mixture was allowed to warm to room temperature. The reaction mixture was then diluted with 500 ml of water and extracted with ethyl ether (3×75 ml). The combined extracts were washed with saturated sodium bicarbonate, brine, dried (MgSO$_4$) and condensed in vacuo to yield 29.9 g of bromomethyl cycloheptyl ketone as an oil.

EXAMPLE 11b

2-Carboethoxy-4-cycloheptylthiazole

A solution composed of 22.9 g of bromomethyl cycloheptyl ketone, 13.0 g of ethyl thiooxamate and 200 ml of ethyl alcohol was heated to reflux for 4 hr afterwhich the volatiles were removed in vacuo and the residual materials were mixed with an excess of saturated sodium bicarbonate solution. This mixture was extracted with methylene chloride and the combined extracts were dried (MgSO$_4$) and condensed in vacuo to give 25.4 g of 2-carboethoxy-4-cycloheptylthiazole as an oil.

EXAMPLE 11c

4-Cycloheptyl-2-thiazolemethanol

Sodium borohydride (6.4 g) was added in one portion to an ice cold solution composed of 25.4 g of 2-carboethoxy-4-cycloheptylthiazole and 200 ml of ethyl alcohol. The ice bath was removed after 30 min and the reaction mixture was allowed to warm to room temperature. After 16 hr the reaction mixture was diluted with 400 ml of ice water and extracted with methylene chloride. The combined extracts were washed with brine, dried (MgSO$_4$) and concentrated in vacuo to yield 18.6 g of 4-cycloheptyl-2-thiazolemethanol as an oil.

EXAMPLE 11d

2-Chloromethyl-4-cycloheptylthiazole

Thionyl chloride (11.4 ml) was added to an ice cold solution of 18.6 g of 4-cycloheptyl-2-thiazolemethanol in 200 ml of methylene chloride. After 5 min the ice bath was removed and the solution allowed to warm to room temperature. After 16 hr, the reaction mixture was condensed in vacuo and the residual materials were mixed with and excess of water and saturated sodium bicarbonate solution. This mixture was extracted with ethyl ether and the combined extracts were washed with brine, dried (MgSO$_4$)and condensed in vacuo to yield 17.8 g of material. Further purification of this material by silica gel chromatography using methylene chloride as the eluant yielded 8.16 g of 2-chloromethyl-4-cycloheptylthiazole as an oil.

EXAMPLE 11e

[4-(Cycloheptyl-2-thiazolyl)methyl]triphenylphosphonium Chloride

A mixture of 8.1 g of 2-chloromethyl-4-cycloheptylthiazole, 9.2 g of triphenylphosphine and 100 ml of toluene was heated to reflux for 48 hr. After cooling to room temperature, the mixture was filtered and the solids mixed with 150 ml of tetrahydrofuran. This mixture was heated to 50° C. for 1 hr, cooled to room temperature and filtered to yield 10 g of [4-(cycloheptyl-2-thiazolyl)methyl]triphenylphosphonium chloride, m.p. 189°–191° C.

EXAMPLE 11f

(E)-4-Cycloheptyl-2-[2-(3-nitrophenyl)ethenyl]thiazole

A suspension of 4.6 g of [4-(cycloheptyl-2-thiazolyl)methyl]triphenylphosphonium chloride in 100 ml of tetrahydrofuran was reacted at room temperature and under a positive argon atmosphere with 1.05 g of potassium tert-butoxide. After 1 hr, 1.4 g of 3-nitrobenzaldehyde was added and the mixture stirred for 2 hr. afterwhich it was diluted with 500 ml of water and extracted with methylene chloride. The combined extracts were washed with brine, dried (MgSO$_4$) and concentrated in vacuo to yield 4.9 g of (E)-4-cycloheptyl-2-[2-(3-nitrophenyl)ethenyl]thiazole.

EXAMPLE 11g

(E)-3-[2-[4-(Cycloheptyl)-2-thiazolyl]ethenyl]benzeneamine

A mixture composed of 5.7 g of (E)-4-cycloheptyl-2-[2-(3-nitrophenyl)ethenyl]thiazole, 60 ml of ethyl alcohol and 13.7 g of tin(II) chloride dihydrate was heated to reflux for 2 hr. The cooled reaction mixture was then diluted with 200 ml of 1.5N sodium hydroxide and this mixture was extracted with ethyl ether. The combined extracts were washed with brine, dried (MgSO$_4$) and condensed in vacuo to yield 7.9 g of residual materials which were separated by silica gel chromatography using ethyl acetate as the eluant to yield 3.9 g of (E)-3-[2-[4-(cycloheptyl)-2-thiazolyl]ethenyl]benzeneamine as an oil.

EXAMPLE 11h

(E)-4-Cycloheptyl-2-[2-(3-nitrophenyl)ethenyl]thiazole

A solution composed of 6.57 g of bromomethyl cycloheptyl ketone, 6.24 g of (E)-3-(3-nitrophenyl)-2-propenethioamide and 100 ml of ethyl alcohol was heated to reflux for 16 hr afterwhich it was diluted with 200 ml of ice water and extracted with methylene chloride. The combined extracts were washed with saturated sodium bicarbonate, brine, dried (MgSO$_4$) and condensed in vacuo to yield 6.17 g of (E)-4-cycloheptyl-2-[2-(3-nitrophenyl)ethenyl]thiazole; m.p. 60° C. after crystallization from ethyl ether/hexane.

EXAMPLE 11i

(E)-2-[2-[3-[2-[4-(Cycloheptyl)-2-thiazolyl]ethenyl]phenylamino]-2-oxoethyl]benzoic acid A solution of 2.1 g of (E)-3-[2-[4-(cycloheptyl)-2-thiazolyl]ethenyl]benzeneamine, 1.25 g of homophthalic anhydride and 30 ml of toluene was heated to reflux for 0.5 hr. Cooling and filtration yielded 2.31 g of (E)-2-[2-[3-[2-[4-(cycloheptyl)-2-thiazolyl]ethenyl]phenyl=amino]-2-oxoethyl]benzoic acid; m.p. 189°–190° C. from tetrahydrofuran.

Anal. Calcd for C$_{27}$H$_{28}$N$_2$O$_3$S: C, 70.41; H, 6.13; N, 6.08. Found: C, 70.43; H, 6.14; N, 6.00.

EXAMPLE 12a

Bromomethyl Cyclooctyl Ketone

An ice cold solution of 5.5 g of cyclooctyl methyl ketone in 50 ml of methyl alcohol was treated dropwise with 1.95 g of bromine. After 5 min, the ice bath was removed and the reaction mixture was allowed to warm to room temperature. The reaction mixture was then diluted with 200 ml of water and extracted with ethyl ether (3×60 ml). The combined extracts were washed with saturated sodium bicarbonate, brine, dried (MgSO$_4$) and condensed in vacuo to yield 6.2 g of bromomethyl cyclooctyl ketone as an oil.

EXAMPLE 12b

(E)-4-Cyclooctyl-2-[2-(3-nitrophenyl)ethenyl]thiazole

A solution composed of 6.2 g of bromomethyl cyclooctyl ketone, 5.6 g of (E)-3-(3-nitrophenyl)-2-propenethioamide and 75 ml of ethyl alcohol was heated to reflux for 1 hr afterwhich it was diluted with 200 ml of ice water and extracted with methylene chloride. The combined extracts were washed with water, dried (MgSO$_4$) and condensed in vacuo to give an oil which was further purified by chromatography over florisil using methylene chloride as the eluant to yield 4.5 g of (E)-4-cyclooctyl-2-[2-(3-nitrophenyl)ethenyl]thiazole; m.p. 64°–65° C. after crystallization from ethyl alcohol.

Anal. Calcd for $C_{19}H_{22}N_2O_2S$: C, 66.64; H, 6.48; N, 8.18. Found: C, 66.47; H, 6.30; N, 8.32.

EXAMPLE 12c (E)-3-[2-[4-(Cyclooctyl)-2-thiazolyl]ethenyl]benzeneamine

A mixture composed of 2.0 g of (E)-4-cyclooctyl-2-[2-(3-nitrophenyl)ethenyl]thiazole, 50 ml of ethyl alcohol and 4.6 g of tin(II) chloride dihydrate was heated to reflux for 1.2 hr. The cooled reaction mixture was then diluted with 200 ml of 1.5N sodium hydroxide and this mixture was extracted with ethyl ether. The combined extracts were washed with brine, dried (MgSO₄) and condensed in vacuo and the residual materials were further purified by silica gel chromatography using ethyl acetate as the eluant to yield 1.8 g of (E)-3-[2-[4-(cyclooctyl)-2-thiazolyl]ethenyl]benzeneamine as an oil.

EXAMPLE 12d (E)-2-[2-[3-[2-[4-(Cyclooctyl)-2-thiazolyl]ethenyl]phenylamino]-2-oxoethyl]benzoic acid A solution of 0.6 g of (E)-3-[2-[4-(cyclooctyl)-2-thiazolyl]ethenyl]benzeneamine, 0.312 g of homophthalic anhydride and 25 ml of toluene was heated to reflux for 0.25 hr. Cooling and filtration yielded 0.5 g of product. Recrystallization from ethyl acetate/acetonitrile yielded (E)-2-[2-[3-[2-[4-(cyclooctyl)-2-thiazolyl]ethenyl]phenylamino]-2-oxoethyl]benzoic acid; m.p. 180°–182° C.

Anal. Calcd for $C_{28}H_{30}N_2O_3S$: C, 70.86; H, 6.37; N, 5.90. Found: C, 70.62; H, 6.43; N, 5.95.

EXAMPLE 13

(E)-2-[2-[3-[2-[4-(Cyclobutyl)-2-thiazolyl]ethenyl]phenylamino]-2-oxoethyl]benzeneacetic acid A solution of 0.64 g of (E)-3-[2-[4-(cyclobutyl)-2-thiazolyl]ethenyl]phenylamine, 0.97 g of 1,2-phenylenediacetic acid, 0.31 g of 4-dimethylaminopyridine, 0.48 g of N-ethyl-N-(dimethylamino) propylcarbodiimide hydrochloride and 50 ml of methylene chloride was stored at room temperature for 18 hr. At this point the reaction solution was washed with water (3×15 ml), 1N hydrochloric acid (15 ml), saturated sodium chloride (15 ml) and then dried (MgSO₄). Rotary evaporation of the resulting solution yielded 0.8 g of product after trituration with ethyl ether. Recrystallization from acetonitrile yielded 0.35 g of (E)-2-[2-[3-[2-[4-(cyclobutyl)-2-thiazolyl]ethenyl]phenylamino]-2-oxoethyl]benzeneacetic acid, m.p. 160°–162° C.

Anal. Calcd for $C_{25}H_{24}N_2O_3S$: C, 69.42; H, 5.59; N, 6.48. Found: C, 69.47; H, 5.64; N, 6.66.

EXAMPLE 14

(E)-2-[2-[3-[2-[4-(1-Methylethyl)-2-thiazolyl]ethenyl]phenylamino]-2-oxoethyl]benzene acetic acid A solution of 0.61 g of (E)-3-[2-[4-(1-methylethyl)-2-thiazolyl]ethenyl]phenylamine, 0.97 g of 1,2-phenylenediacetic acid, 0.31 g of 4-dimethylaminopyridine, 0.48 g of N-ethyl-N-(dimethylamino)propylcarbodiimide hydrochloride and 50 ml of methylene chloride was stored at room temperature for 18 hr. At this point the reaction solution was washed with water (3×15 ml), 1N hydrochloric acid (15 ml), saturated sodium chloride (15 ml) and then dried (MgSO₄). Rotary evaporation of the resulting solution yielded 0.7 g of product after trituration with ethyl ether. Recrystallization from acetonitrile yielded (E)-2-[2-[3-[2-[4-(1-methylethyl)-2-thiazolyl]ethenyl]phenylamino]-2-oxoethyl]benzeneacetic acid, m.p. 144°–146° C.

Anal. Calcd for $C_{24}H_{24}N_2O_3S$: C, 68.55; H, 5.75; N, 6.66. Found: C, 68.65; H, 5.69; N, 6.96.

EXAMPLE 15

(E)-3-[2-[3-[2-[4-(1-Methylethyl)-2-thiazolyl]ethenyl]phenylamino]-2-oxoethyl]phenylacetic acid A solution of 0.61 g of (E)-3-[2-[4-(1-methylethyl)-2-thiazolyl]ethenyl]phenylamine, 0.97 g of 1,3-phenylenediacetic acid, 0.31 g of 4-dimethylaminopyridine, 0.48 g of N-ethyl-N-(dimethylamino)propylcarbodiimide hydrochloride and 50 ml of methylene chloride was stored at room temperature for 18 hr. At this point the reaction solution was washed with water (3×15 ml), 1N hydrochloric acid (15 ml), saturated sodium chloride (15 ml) and then dried (MgSO₄). Rotary evaporation of the resulting solution yielded 0.8 g of product after trituration with ethyl ether. Recrystallization from acetonitrile yielded 0.4 g of (E)-3-[2-[3-[2-[4-(1-methylethyl) -2-thiazolyl]ethenyl]phenylamino]-2-oxoethyl]phenylacetic acid; m.p. 122°–124° C.

Anal. Calcd for $C_{24}H_{24}N_2O_3S$: C, 68.55; H, 5.75; N, 6.66. Found: C, 68.15; H, 5.93; N, 6.75.

EXAMPLE 16a

2-Carboethoxy-4-(1-methylethyl)thiazole

A solution composed of 5.0 g of 1-bromo-3-methyl-2-butanone, 4.4 g of ethyl thiooxamate and 100 ml of ethyl alcohol was heated to reflux for 16 hr afterwhich the volatiles were removed in vacuo and the residual materials were mixed with an excess of saturated sodium bicarbonate solution. This mixture was extracted with methylene chloride and the combined extracts were dried (MgSO₄) and condensed in vacuo to give 4.8 g of 2-carboethoxy-4-(1-methylethyl)thiazole.

EXAMPLE 16b 4-(1-Methylethyl)-2-thiazole methanol

A solution of 4.5 g of 2-carboethoxy-4-(1-methylethyl)thiazole, 100 ml of ethyl alcohol and 1.1 g of sodium borohydride was heated to reflux for 4 hr. The reaction mixture was then condensed to one half of the original volume in vacuo, diluted with 150 ml of water and extracted with methylene chloride. The combined extracts were washed with water, dried (MgSO₄) and condensed in vacuo to give 4.0 g of 4-(1-methylethyl)-2-thiazole methanol; m.p. 80°–82° C.

EXAMPLE 16c

2-Iodomethyl-4-(1-methylethyl)thiazole

A mixture composed of 2.5 g of 4-(1-methylethyl)thiazole methanol, 6.3 g of triphenylphosphine, 2.2 g of imidazole and 100 ml of toluene was warmed until all of the solids dissolved. This solution was cooled to 10° C. and 6.1 g of iodine was added. After 2 hr, the mixture was washed with an excess of sodium thiosulfate solution. The aqueous layer was back extracted with ethyl ether and the combined organic layers were washed with brine and then dried (MgSO₄). Removal of the solvents in vacuo yielded 5.0 g of 2-iodomethyl-4-(1-methylethyl)thiazole as an oil.

EXAMPLE 16d

[4-(1-Methylethyl)-2-thiazolyl)methyl]triphenylphosphonium iodide

A mixture of 5.0 g of 2-iodomethyl-4-(1-methylethyl)thiazole, 4.7 g of triphenylphosphine and 100 ml of toluene was heated to 90° C. for 0.5 hr. After cooling to room temperature, the mixture was filtered and the solids washed with ethyl ether to yield 5.4 g of [4-(1-methylethyl-2-thiazolyl)methyl]triphenylphosphonium iodide.

EXAMPLE 16e (E)-4-(1-Methylethyl)-2-[2-(2-methyl-5-nitrophenyl)ethenyl]thiazole A mixture of 1.6 g of [4-(1-methylethyl-2-thiazolyl)methyl]triphenylphosphonium iodide in 35 ml of tetrahydrofuran was sealed under a positive of argon atmosphere and reacted dropwise with 1.9 ml of 1.6M n-butyllithium in hexane. After 1 hr, a solution composed of 0.5 g of 2-methyl-5-nitrobenzaldehyde in 15 ml of tetrahydrofuran was added. After 2 hr the mixture was condensed in vacuo and the residual materials were separated by silica gel chromatography using ethyl acetate-hexane (1:9 v/v) to yield 1.9 g of (E)-4-(1-methylethyl)-2-[2-(2-methyl-5-nitrophenyl)ethenyl]thiazole; m.p. 87°–88° C.

Anal. Calcd for $C_{15}H_{16}N_2O_2S$: C, 62.48; H, 5.59; N, 9.71; S 11.12. Found: C, 62.09; H, 5.55; N, 9.66; S 10.79.

EXAMPLE 16f (E)-4-Methyl-3-[2-[4-(1-methylethyl)-2-thiazolyl]ethenyl]benzenamine A solution of 1.2 g of (E)-4-(1-methylethyl)-2-[2-(2-methyl-5-nitrophenyl)ethenyl]thiazole, 3.2 g of tin(II) chloride dihydrate and 50 ml of ethyl alcohol was heated to reflux for 2 hr. The reaction mixture was cooled in an ice bath and then diluted with 50 ml of 3N sodium hydroxide. This mixture was extracted with ethyl acetate, dried (MgSO$_4$) and condensed in vacuo to yield 1.2 g of (E)-4-methyl-3-[2-[4-(1-methylethyl)-2-thiazolyl]ethenyl]benzenamine; m.p. 60°–61° C. from hexane.

Anal. Calcd for $C_{15}H_{18}N_2S$: C, 69.73; H, 7.02; N, 10.84; S 12.41. Found: C, 69.90; H, 6.97; N, 10.81; S 12.53.

EXAMPLE 16g (E)-2-[2-[4-Methyl-3-[2-[4-(1-methylethyl)-2-thiazolyl]ethenyl]phenylamino]-2-oxoethyl]benzoic acid A mixture of 0.5 g of (E)-4-methyl-3-[2-[4-(1-methylethyl)-2-thiazolyl]ethenyl]benzenamine, 0.5 g of homophthalic anhydride and 35 ml of toluene was heated to reflux for 1 hr. After cooling and dilution with hexane, 0.5 g of (E)-2-[2-[4-methyl-3-[2-[4-(1-methylethyl)-2-thiazolyl]ethenyl]phenylamino]-2-oxoethyl]benzoic acid was isolated by filtration; m.p. 181°–183° C.

EXAMPLE 17a (E)-3-(2-Chloro-5-nitrophenyl)-2-propenamide

A mixture of 10 g of (E)-3-(2-chloro-5-nitrophenyl)-2-propenoic acid and 50 ml of thionyl chloride was warmed to reflux for 5 hr. The excess of thionyl chloride was removed in a vacuo with toluene flushing (2x) afterwhich the residual materials were mixed at 0° C. with concentrated ammonium hydroxide to form (E)-3-(2-chloro-5-nitrophenyl)-2-propenamide; m.p. 208°–210° C. after recrystallization from acetonitrile.

Anal. Calcd for $C_9H_7ClN_2O_3$: C, 47.70; H, 3.11; N, 12.36. Found: C, 47.37; H, 3.03; N, 12.27.

EXAMPLE 17b (E)-3-(2-Chloro-5-nitrophenyl)-2-propenethioamide

A solution composed of 5.0 g of (E)-3-(2-chloro-5-nitrophenyl)-2-propenamide, 4.4 g of Lawesson's reagent and 100 ml of tetrahydrofuran was stirred under a positive argon atmosphere at room temperature for 16 hr. The volatiles were then removed in vacuo and the residual materials slurried with 100 ml of methylene chloride to yield (E)-3-(2-chloro-5-nitrophenyl)-2-propenethioamide as a orange solid; m.p. 236°–238° C. from acetonitrile.

Anal. Calcd for $C_9H_7ClN_2O_2S$: C, 44.50; H, 2.90; N, 11.54. Found: C, 43.98; H, 2.81; N, 11.38.

EXAMPLE 17c (E)-2-[2-(2-Chloro-5-nitrophenyl)ethenyl]-4-(1-methylethyl)thiazole A solution composed of 2.0 g of (E)-3-(2-chloro-5-nitrophenyl)-2-propenethioamide, 3.0 g of 1-bromo-3-methyl-2-butanone and 25 ml of ethyl alcohol was warmed to gentle reflux for 5 hr. The volatiles were then removed in vacuo and the residual materials separated by chromatography over 100 g of alumnia using methylene chloride as the eluant to yield (E)-2-[2-(2-chloro-5-nitrophenyl)ethenyl]-4-(1-methylethyl)-thiazole as a yellow solid; m.p. 86°–89° C.

Anal. Calcd for $C_{14}H_{13}ClN_2O_2S$: C, 54.46; H, 4.24; N, 9.07. Found: C, 54.37; H, 4.23; N, 9.08.

EXAMPLE 17d (E)-2-[2-(5-Amino-2-chlorophenyl)ethenyl]-4-(1-methylethyl)thiazole A solution composed of 3.0 g of (E)-2-[2-(2-chloro-5-nitrophenyl)ethenyl]-4-(1-methylethyl)thiazole, 8.0 g of tin(II) chloride dihydrate and 100 ml of ethyl alcohol was heated to reflux for 1 hr. The reaction mixture was then condensed to half of its original volume, diluted with ice water, basified with 3N sodium hydroxide and extracted with methylene chloride. The combined extracts were washed with water and brine, dried (MgSO$_4$)and condensed in vacuo to yield (E)-2-[2-(5-amino-2-chlorophenyl)ethenyl]-4-(1-methylethyl)-thiazole; m.p. 82°–85° C. from hexane.

Anal. Calcd for $C_{14}H_{15}ClN_2S$: C, 60.31; H, 5.42; N, 10.05. Found: C, 59.64; H, 5.37; N, 9.80.

EXAMPLE 17e (E)-2-[2-[4-Chloro-3-[2-[4-(1-methylethyl)-2-thiazolyl]ethenyl]phenylamino]-2-oxoethyl]benzoic acid A solution of 1.28 g of (E)-[4-chloro-3-[-2-[4-(1-methylethyl)-2-thiazolyl]ethenyl]]benzeneamine, 0.81 g of homophthalic anhydride, 50 ml of toluene and 25 ml of tetrahydrofuran was heated to reflux for 0.5 hr. The solvents were removed by rotary evaporation and the residual materials were triturated with ethyl ether to yield 1.15 g of product. Recrystallization from acetonitrile yielded 0.81 g of (E)-2-[2-[4-chloro-3-[2-[4-(1-methylethyl)-2-thiazolyl]ethenyl]phenylamino]-2-oxoethyl]benzoic acid; m.p. 204°–206° C. from ethyl acetate-/ethyl alcohol.

Anal. Calcd for $C_{23}H_{21}N_2O_3S$: C, 62.05; H, 4.80; N, 6.35. Found: C, 61.95; H, 4.83; N, 6.07.

EXAMPLE 18a (E)-2-[2-(3-Nitrophenyl)ethenyl]-4-thiazolecarboxylic Acid Ethyl Ester A solution of 3.9 g of ethyl bromopyruvate, 4.2 g of m-nitrothiocinnamide and 100 ml of ethanol was heated to reflux for 1 hr. The reaction mixture was poured into ice-water and extracted with methylene chloride. The methylene chloride solution was washed with water, dried (MgSO$_4$) and the solvent evaporated in vacuo to yield 6.0 g of (E)-2-[2-(3-nitrophenyl)ethenyl]-4-thiazolecarboxylic acid ethyl ester; m.p. 151°–153° C. from ethyl acetate.

Anal. Calcd for $C_{14}H_{12}N_2O_4S$: C, 55.26; H, 3.97; N, 9.21. Found: C, 55.38; H, 3.88; N, 9.14.

EXAMPLE 18b (E)-2-[2-(3-Aminophenyl)ethenyl]-4-thiazolecarboxylic Acid Ethyl Ester A solution of 1.5 g of (E)-2-[2-(3-nitrophenyl)ethenyl]-4-thiazolecarboxylic acid ethyl ester, 3.87 g of tin(II) chloride monohydrate and 100 ml of ethanol was heated to reflux for 16 hr. The reaction mixture was then poured onto ice-water, basified with ammonium hydroxide and extracted with methylene chloride. The methylene chloride solution was washed with water, saturated brine and dried (MgSO$_4$). Evaporation of the solvent in vacuo yielded 1.1 g of (E)-2-[2-(3-aminophenyl)ethenyl]-4-thiazolecarboxylic acid ethyl ester; m.p. 112°–113° C. from ethanol.

Anal. Calcd for $C_{14}H_{14}N_2O_2S$: C, 61.29; H, 5.14; N, 10.21. Found: C, 60.61; H, 5.08; N, 9.91.

EXAMPLE 18c (E)-2-[2-[3-[2-[4-(Ethoxycarbonyl)-2-thiazolyl]ethenyl]-phenylamino]-2-oxoethyl]benzoic acid A solution of 0.5 g of (E)-2-[2-(3-aminophenyl)ethenyl]-4-thiazolecarboxylic acid ethyl ester, 0.3 g of homophthalic anhydride, 15 ml of toluene and 5 ml of tetrahydropyran was heated to reflux for 0.5 hr. Upon cooling, a solid formed which was filtered to yield 0.8 g of (E)-2-[2-[3-[2-[4-(ethoxycarbonyl)-2-thiazolyl]ethenyl]phenylamino]-2-oxoethyl]benzoic acid; m.p. 221°–223° C. from ethanol.

Anal. Calcd for $C_{23}H_{20}N_2O_5S$: C, 63.29; H, 4.62; N, 6.42. Found: C, 62.99; H, 4.58; N, 6.40.

EXAMPLE 19

(E)-2-[2-[3-[(2-Carboxyphenyl)-1-oxoethyl]amino]-phenyl]ethenyl]-4-thiazolecarboxylic acid A mixture of 0.436 g of (E)-2-[2-[3-[2-[4-(ethoxycarbonyl)-2-thiazolyl]ethenyl]phenylamino]-2-oxoethyl]-benzoic acid, 0.168 g of lithium hydroxide and 25 ml of tetrahydro-furan/water (4:1 v/v) was heated on a steambath for 4 hr. The solvents were removed in vacuo and the residual materials were solubilized in water. Acidification of this solution with acetic acid yielded 0.4 g of (E)-2-[2-[3-[[2-carboxyphenyl)-1-oxoethyl]amino]phenyl]ethenyl]-4-thiazolecarboxylic acid after filtration and washing with water; m.p. 141°–143° C. after recrystallization from ethanol.

Anal. Calcd for $C_{21}H_{16}N_2O_5S$: C, 61.76; H, 3.95; N, 6.86. Found: C, 60.69; H, 4.13; N, 6.89.

EXAMPLE 20a

Cyclobutancarbothioamide

A mixture of 13.5 g of cyclobutanecarboxamide, 27.5 g of Lawesson's reagent and 500 ml of tetrahydrofuran was heated to reflux for 16 hr. The volatile components were then removed in vacuo and the residual materials separated by chromatography over florisil using ethyl acetate as the eluant to yield 9.7 g of cyclobutancarbothioamide; m.p. 61°–64° C.

EXAMPLE 20b

2-Cyclobutyl-4-thiazolecarboxylic Acid Ethyl Ester

A mixture composed of 9.7 g of cyclobutancarbothioamide, 16.5 g of ethyl bromopyruvate and 200 ml of ethyl alcohol was heated to reflux for 1 hr. The reaction mixture was partially condensed in vacuo and the residual materials were diluted with ice water and and excess of saturated sodium bicarbonate solution. The solids were collected to yield 7.0 g of 2-cyclobutyl-4-thiazolecarboxylic acid ethyl ester; m.p. 48°–50° C. after recrystallization from pentane.

Anal. Calcd for $C_{10}H_{13}NO_2S$: C, 56.85; H, 6.20; N, 6.63. Found: C, 56.59; H, 6.12; N, 6.48.

EXAMPLE 20c

2-Cyclobutyl-4-thiazole methanol

Sodium borohydride (2.3 g) was added in portions over a 10 min period to an ice cold solution of 6.3 g of 2-cyclobutyl-4-thiazolecarboxylic acid ethyl ester in 100 ml of ethyl alcohol. The ice bath was removed and the reaction mixture stirred at room temperature for 30 hr during which an additional 0.46 g of sodium borohydride was added. The reaction mixture was then diluted with 200 ml of ice water and extracted with ethyl ether. The combined extracts were washed with water, dried (MgSO$_4$) and condensed in vacuo to yield 5.1 g of 2-cyclobutyl-4-thiazole methanol as an oil.

EXAMPLE 20d

4-Chloromethyl-2-cyclobutyl-thiazole

A solution of 5.1 g of 2-cyclobutyl-4-thiazole methanol, 5 ml of thionyl chloride and 100 ml of methylene chloride was stirred at room temperature for 2 hr. The volatiles were removed in vacuo and the residual materials were taken up in 100 ml of methylene chloride, washed with sodium bicarbonate, water, brine, dried (MgSO$_4$) and condensed in vacuo to yield 6 g of dark colored oil. This material was further purified by chromatography over florisil using ethyl acetate/methylene chloride (1:1 v/v) as the eluant to yield 4.8 g of 4-chloromethyl-2-cyclobutyl-thiazole as an oil.

EXAMPLE 20e

[(2-cyclobutyl-4-thiazolyl)methyl]triphenylphosphonium chloride

A mixture of 4.8 g of 4-chloromethyl-2-cyclobutyl-thiazole, 7.0 g of triphenylphosphine and 125 ml of toluene was heated to reflux for 16 hr and then cooled to room temperature. The mixture was then filtered to yield 4.8 g of [(2-cyclobutyl-4-thiazolyl)methyl]=triphenylphosphonium chloride.

EXAMPLE 20f (E)-2-Cyclobutyl-4-[2-(3-nitrophenyl)ethenyl]thiazole

A slurry of 1.8 g of [(2-cyclobutyl-4-thiazolyl)methyl]triphenylphosphonium chloride, in 80 ml of tetrahydrofuran was sealed under a positive argon atmosphere and the mixture cooled with an ice bath. Sodium hydride (0.2 g; 50% oil dispersion) was added and stirring and cooling continued for 30 min afterwhich 0.6 g of 3-nitrobenzaldehyde was added. The cooling bath was removed and the mixture was stirred at room temperature for 1 hr. The mixture was then filtered, condensed in vacuo and the residual materials taken up in 100 ml of methylene chloride. This solution was then washed with water, dried (MgSO$_4$) and condensed in vacuo to yield 0.8 g of (E)-2-cyclobutyl-4-[2-(3-nitrophenyl)ethenyl]thiazole; m.p. 112°–115° C.

EXAMPLE 20g (E)-3-[2-[2-Cyclobutyl-4-thiazolyl]ethenyl]phenylamine

A mixture of 0.3 g of (E)-2-cyclobutyl-4-[2-(3-nitrophenyl)ethenyl]thiazole, 0.9 g of tin(II) chloride dihydrate and 50 ml of ethyl alcohol was heated to reflux for 16 hr. The mixture was then diluted with ice water and an excess of 3N sodium hydroxide. This mixture was extracted with methylene chloride and the combined extracts were washed with water followed with brine and then dried (MgSO$_4$). Condensation in vacuo yielded 0.3 g of (E)-3-[2-[2-Cyclobutyl-4-thiazolyl]ethenyl]phenylamine.

EXAMPLE 20h (E)-2-[2-[3-[2-(2-Cyclobutyl-4-thiazolyl)ethenyl]phenylamino]-2-oxoethyl]benzoic acid A mixture of 0.13 g of (E)-3-[2-[2-cyclobutyl-4-thiazolyl]ethenyl]phenylamine, 0.094 g of homophthalic anhydride and 10 ml of toluene was heated on a steam bath for 1 hr and then allowed to cool to room temperature. Filtration of the reaction mixture yielded 0.1 g of (E)-2-[2-[3-[2-(2-cyclobutyl-4-thiazolyl)ethenyl]phenylamino]-2-oxoethyl]benzoic acid; m.p. 198°–199° C. from acetonitrile.

Anal. Calcd for C$_{24}$H$_{22}$N$_2$O$_3$S: C, 68.88; H, 5.30; N, 6.69. Found: C, 67.98; H, 5.35; N, 6.55.

EXAMPLE 21a (E)-2-[3-[3-[2-[4-(Cyclobutyl)-2-thiazolyl]ethenyl]-phenylamino]-3-oxopropyl]benzoic Acid Ethyl Ester A solution composed of 0.44 g of 2-(ethoxycarbonyl)-benzenepropanoic acid and 25 ml of methylene chloride was added to a solution composed of 0.51 g of (E)-3-[2-[4-(cyclobutyl)-2-thiazolyl]ethenyl]benzeneamine, 0.4 g of N-ethyl-N-(dimethylaminopropyl)carbodiimide, 1.0 g of 4-dimethylaminopyridine and 25 ml of methylene chloride at 0° C. After 16 hr., the reaction mixture was washed with 30 ml of water, dried (MgSO$_4$) and the solvents removed by rotary evaporation. The residual materials were recrystallized from ethyl ether to yield 0.87 g of (E)-2-[3-[3-[2-[4-(cyclobutyl)-2-thiazolyl]ethenyl]phenylamino]-3-oxopropyl]benzoic acid ethyl ester; m.p.110°14 111° C.

Anal. Calcd for C$_{24}$H$_{22}$N$_2$O$_3$S: C, 68.88; H, 5.30; N, 6.69; S, 6.96. Found: C, 70.30; H, 6.09; N, 5.88; S, 6.90.

EXAMPLE 21b (E)-2-[3-[3-[2-[4-(Cyclobutyl)-2-thiazolyl]ethenyl]-phenylamino-]-3-oxopropyl]benzoic acid A solution composed of 0.457 g of (E)-2-[3-[3-[2-[4-(cyclobutyl)-2-thiazolyl]ethenyl]phenylamino]-3-oxopropyl]benzoic acid ethyl ester, 25 ml of tetrahydropyran, 8 ml of methanol, 8 ml of water and 0.282 g of lithium hydroxide monohydrate was allowed to stand at room temperature for 20 hr. The solvents were removed by rotary evaporation and the residual materials were taken up in 30 ml of water. Addition of excess acetic acid caused the precipitation of 0.42 g of (E)-2-[3-[3-[2-[4-(cyclobutyl)-2-thiazolyl]ethenyl]phenylamino]-3-oxopropyl]benzoic acid; m.p. 238°–239° C.

EXAMPLE 22a (E)-3-[2-[4-(Cyclobutyl)-2-thiazolyl]ethenyl]benzenecarboxaldehyde A slurry composed of 27.05 g [(2-cyclobutyl-4-thiazolyl)methyl]triphenylphosphonium iodide and 300 ml of tetrahydrofuran was sealed under a positive argon atmosphere and cooled in an ice bath. Potassium tert-butoxide (6.2 g) was added in one portion afterwhich the ice bath was removed and the mixture stirred at room temperature for 2 hr. This mixture was then added to a solution of 6.7 g of isophthalaldehyde in 100 ml of tetrahydrofuran and the reaction mixture was kept at room temperature for 16 hr. The reaction mixture was then concentrated in vacuo to approximately one quarter of its original volume and the residual materials were diluted with 300 ml of water. This mixture was extracted with ethyl ether and the combined extracts were washed with water, brine, dried (MgSO$_4$) and concentrated in vacuo. The residual materials were mixed with a small volume of ethyl ether-hexane (1:1 v/v), filtered and the filtrate further purified by silica gel chromatography using ethyl acetate-hexane (1:7 v/v) as the eluant to yield 12.2 g of (E)-3-[2-[4-(cyclobutyl)-2-thiazolyl]ethenyl]benzenecarboxaldehyde; m.p. 78°–80° C.

EXAMPLE 22b (E)-3-[2-(4-Cyclobutyl)-2-thiazolyl)ethenyl]benzoic acid

A mixture composed of 3.15 g of (E)-3-[2-[4-(cyclobutyl)-2-thiazolyl]ethenyl]benzenecarboxaldehyde, 1.44 g of potassium tert-butoxide and 100 ml of tert-butanol was heated to reflux for 2 hr while exposed to air. The mixture was then diluted with 100 ml of ice water. This mixture was then acidified with acetic acid and extracted with methylene chloride. The combined extracts were washed with water, brine, dried (MgSO$_4$) and concentrated in vacuo to yield (E)-3-[2-(4-cyclobutyl)-2-thiazolyl)ethenyl]benzoic acid; m.p. 172°–175° C. from ethyl acetate.

Anal. Calcd for C$_{16}$H$_{15}$NO$_2$S: C, 67.33; H, 5.29; N, 4.90. Found: C, 67.46; H, 5.13; N, 4.65.

EXAMPLE 22c (E)-2-[[[[3-[2-(4-Cyclobutyl-2-thiazolyl)ethenyl]-phenyl]carbonyl]amino]methyl]benzoic acid A mixture composed of 1.3 g of (E)-3-[2-(4-cyclobutyl)-2-thiazolyl)ethenyl]benzoic acid, 0.45 ml of oxalyl chloride, 40 ml of methylene chloride and 0.3 ml of dimethylformamide was stirred at room temperature for 16 hr. The mixture was then condensed in vacuo. A portion (0.6 g) of the residual materials was mixed with a solution composed of 50 ml of dimethylformamide, 0.37 g of 2-(aminomethyl)-benzoic acid, and 0.51 g of triethylamine and stirred at room temperature. After 3 hr, the mixture was washed with water, dried (MgSO$_4$) and condensed in vacuo. The residual materials were separated by silica gel chromatography to yield (E)-2-[[[[3-[2-(4-cyclobutyl-2 -thiazolyl)ethenyl]phenyl]carbonyl]amino]methyl]benzoic acid; m.p. 185°–187° C. from ethyl acetate.

EXAMPLE 23

(E)-5-Nitro-2-[2-[3-[2-[4-(cyclobutyl)-2-thiazolyl]ethenyl]phenylamino]-2-oxoethyl]benzoic acid A solution of 0.4 g of (E)-3-[2-[4-(cyclobutyl)-2-thiazolyl]ethenyl]benzeneamine, 1.0 g of 5-nitrohomophthalic anhydride and 50 ml of toluene and 10 ml of tetrahydrofuran was heated to reflux for 0.5 hr. The solvents were removed by rotary evaporation and the residual materials were triturated with acetonitrile to yield (E)-5-nitro-2-[2-[3-[2-[4-(cyclobutyl)-2-thiazolyl]ethenyl]phenylamino]-2-oxoethyl]benzoic acid, m.p. 233°–235° C.

Anal. Calcd for $C_{24}H_{21}N_3O_5S$: C, 62.22; H, 4.56; N, 9.07; S, 6.92. Found: C, 62.12; H, 4.45; N, 9.04; S, 6.83.

EXAMPLE 24

(E)-5-Chloro-2-[2-[3-[2-[4-(cyclobutyl)-2-thiazolyl]ethenyl]phenylamino]-2-oxoethyl]benzoic acid A solution of 0.65 g of (E)-3-[2-[4-(cyclobutyl)-2-thiazolyl]ethenyl]benzeneamine, 0.5 g of 5-chlorohomophthalic anhydride and 50 ml of toluene was heated to reflux for 0.5 hr. The solvents were removed by rotary evaporation and the residual materials were triturated with ethanol to yield (E)-5-chloro-2-[2-[3-[2-[4-(cyclobutyl)-2-thiazolyl]ethenyl]phenylamino]-2-oxoethyl]benzoic acid; m.p. 223°–225° C.

Anal. Calcd. for $C_{24}H_{21}ClN_2O_3S$: C, 63.64; H, 4.67; N, 6.18; S, 7.08; Cl, 7.83. Found: C, 63.36; H, 4.83; N, 6.00; S, 6.92; Cl, 7.66.

EXAMPLE 25

(E)-3-Fluoro-2-[2-[3-[2-[4-(cyclobutyl)-2-thiazolyl]ethenyl]phenylamino]-2-oxoethyl]benzoic acid A solution of 0.326 g of (E)-3-[2-[4-(cyclobutyl)-2-thiazolyl]ethenyl]benzeneamine, 0.255 g of 3-fluorohomophthalic anhydride and 25 ml of toluene was heated to reflux for 0.5 hr. The solvents were removed by rotary evaporation and the residual materials were triturated with acetonitrile to yield (E)-3-fluoro-2-[2-[3-[2-[4-(cyclobutyl)-2-thiazolyl]ethenyl]phenylamino]-2-oxoethyl]benzoic acid, m.p. 221°–222° C.

Anal. Calcd. for $C_{24}H_{21}FN_2O_3S$: C, 66.03; H, 4.85; N, 6.42; S, 7.35; F, 4.35. Found: C, 65.89; H, 4.73; N, 6.35; S, 7.37; F, 4.53.

EXAMPLE 26

(E)-5-Methoxy-2-[2-[3-[2-[4-(cyclobutyl)-2-thiazolyl]ethenyl]-phenylamino]-2-oxoethyl]benzoic acid A solution of 0.4 g of (E)-3-[2-[4-(cyclobutyl)-2-thiazolyl]ethenyl]benzeneamine, 0.4 g of 5-methoxyhomophthalic anhydride, 50 ml of toluene and 10 ml of tetrahydrofuran was heated to reflux for 0.5 hr. The solvents were removed by rotary evaporation and the residual materials were triturated with ethanol to yield (E)-5-methoxy-2-[2-[3-[2-[4-(cyclobutyl)-2-thiazolyl]ethenyl]phenylamino]-2-oxoethyl]benzoic acid, m.p. 190°–191° C.

EXAMPLE 27

(E)-5-Fluoro-2-[2-[3-[2-[4-(cyclobutyl)-2-thiazolyl]ethenyl]phenylamino]-2-oxoethyl]benzoic acid A solution of 0.326 g of (E)-3-[2-[4-(cyclobutyl)-2-thiazolyl]ethenyl]benzeneamine, 0.255 g of 3-methoxyhomophthalic anhydride and 25 ml of toluene was heated to reflux for 0.5 hr. The solvents were removed by rotary evaporation and the residual materials were triturated with acetonitrile to yield (E)-5-fluoro-2-[2-[3-[2-[4-(cyclobutyl)-2-thiazolyl]ethenyl]phenylamino]-2-oxoethyl]benzoic acid; m.p. 211°–212° C.

Anal. Calcd. for $C_{24}H_{21}FN_2O_3S$; C, 66.03; H, 4.85; N, 6.42; S, 7.35; F, 4.35. Found C, 65.76; H, 4.68; N, 6.40; S, 7.33; F, 4.46.

EXAMPLE 28a (E)-4-[2-[3-[2-(4-Cyclobutyl)-2-thiazolyl]ethenyl]-phenylamino]-2-oxoethyl]-3-Methoxybenzoic Acid Methyl Ester A solution composed of 0.49 g of (E)-3-[2-[4-(cyclobutyl)-2-thiazolyl]ethenyl]benzeneamine, 0.43 g of 4-carboxymethyl-3-methoxybenzoic acid methyl ester, 0.4 g of N-ethyl-N-(dimethylaminopropyl)carbodiimide and 25 ml of methylene chloride was sealed in a flask and stored at 25° C. for 16 hr. The reaction mixture was then washed with 10 ml of water, dried (MgSO$_4$) and the solvent removed by rotary evaporation. The residual material was purified by silica gel chromatography using ethyl acetate as the eluant to yield 0.62 g of (E)-4-[2-[3-[2-(4-cyclobutyl)-2-thiazolyl]ethenyl]-phenylamino]-2-oxoethyl]-3-methoxybenzoic acid methyl ester; m.p., 156°–157° C. from ethyl acetate.

Anal. Calcd. for $C_{26}H_{26}N_2O_4S$: C, 67.51; H, 5.67; N, 6.06; S, 6.93; Found: C, 67.29; H, 5.63; N, 5.91; S, 6.69.

EXAMPLE 28b (E)-4-[2-[3-[2-[4-(cyclobutyl)-2-thiazolyl]ethenyl]-phenylamino]-2-oxoethyl]-3-methoxybenzoic acid A solution of 0.57 g of (E)-4-[2-[3-[2-[4-(cyclobutyl)-2-thiazolyl]ethenyl]phenylamino]-2-oxoethyl]-3-methoxybenzoic acid methyl ester, 25 ml of tetrahydrofuran, 8 ml of methanol and 0.28 g of lithium hydroxide monohydrate was stored at 25° C. for 20 hr. The solvents were removed by rotary evaporation and the residual materials solubilized in 50 ml of water. Acetic acid was added and the precipitate of (E)-4-[2-[3-[2-[4-(cyclobutyl)-2-thiazolyl]ethenyl]phenylamino]-2-oxoethyl]-3-methoxybenzoic acid was isolated by filtration, m.p. 242°–243° C. after trituration with hot acetonitrile.

Anal. Calcd. for $C_{25}H_{24}N_2O_4S$: C, 66.94; H, 5.39; N, 6.25; S, 7.15; Found: C, 66.75; H, 5.38; N, 6.48; S, 7.22.

EXAMPLE 29

(E)-2-[2-[3-[2-[4-(Cyclobutyl)-2-thiazolyl]ethenyl]-phenylamino]-2-oxoethyl]benzoic acid sodium salt A solution of 0.418 g of (E)-2-[2-[3-[2-[4-(cyclobutyl)-2-thiazolyl]ethenyl]phenylamino]-2-oxoethyl]benzoic acid in 10 ml of ethyl alcohol was mixed at room temperature with 5.0 ml of 0.2N sodium hydroxide solution. This mixture was warmed on a steam bath until all the solids had solubilized. After cooling the reaction mixture was condensed in vacuo at 40° C. to constant weight to yield E)-2-[2-[3-[2-[4-(cyclobutyl)-2-thiazolyl]ethenyl]phenylamino]-2-oxoethyl]benzoic acid sodium salt as a white solid.

EXAMPLE 30

(E)-2-[2-[3-[2-[4-(Cyclobutyl)-2-thiazolyl]ethenyl]-phenylamino]-2-oxoethyl]benzoic Acid Tris-(hydroxymethyl)-amino-methane salt A mixture of 0.418 g of (E)-2-[2-[3-[2-[4-(cyclobutyl)-2-thiazolyl]ethenyl]phenylamino]-2-oxoethyl]benzoic acid and 0.1214 g of tris-(hydroxymethyl)-aminomethane were solubilized in 10 ml of ethyl alcohol with warming on a steam bath until all the solids had solubilized. After cooling the reaction mixture was condensed in vacuo at 40° C. to constant weight to yield E)-2-[2-[3-[2-[4-(cyclobutyl)-2-thiazolyl]ethenyl]phenylamino]-2-oxoethyl]benzoic acid tris-(hydroxymethyl)-aminomethane salt as a white solid.

EXAMPLE 31

(E)-5-Acetoxy-2-[2-[3-[2-[4-(cyclobutyl)-2-thiazolyl]ethenyl]phenylamino]-2-oxoethyl]benzoic Acid.

A mixture composed of 0.58g of (E)-3-[2-[4-(cyclobutyl)-2-thiazolyl]ethenyl]benzeneamine, 0.48g of 5-acetoxyhomophthalic anhydride and 50 ml of toluene was heated on a steam bath for 0.5 hr. The mixture was cooled and the solids that formed were isolated by filtration to yield 0.77 g of (E)-5-acetoxy-2-[2-[3-[2-[4-(cyclobutyl)-2-thiazolyl]ethenyl]phenylamino]-2-oxoethyl]benzoic acid; m.p. 176°–179° C. after trituration with hot acetonitrile.

Anal. Calcd. for $C_{26}H_{24}N_2O_5S$: C, 65.53; H, 5.08; N, 5.88. Found: C, 65.45; H, 4.84; N, 5.99.

EXAMPLE 32

In a similar manner to Example 7a and 7b, when 2-carbomethoxy-1-methylbenzene acetic acid is reacted with (E)-3-[2-[4-(cyclobutyl)-2-thiazolyl]ethenyl]benzeneamine, there is obtained (E)-2-[2-[3-[2-[4-(cyclobutyl)-2-thiazolyl]ethenyl]phenylamino-1-methyl-2-oxoethyl]benzoic acid methyl ester which is converted to (E)-2-[2-[3-[2-[4-(cyclobutyl)-2-thiazolyl]ethenyl]-phenylamino-1-methyl-2-oxoethyl]benzoic acid.

EXAMPLE 33

In a manner analogous to Example 7a and 7b, when 2-carbomethoxy-1,1-dimethylbenzene acetic acid is reacted with (E)-3-[2-[4-(cyclobutyl)-2-thiazolyl]ethenyl]-benzeneamine, there is obtained (E)-2-[2-[3-[2-[4-(cyclobutyl)-2-thiazolyl]ethenyl]phenylamino]-1,1-dimethyl-2-oxoethyl]benzoic acid methyl ester which is converted to (E)-2-[2-[3-[2-[4-(cyclobutyl)-2-thiazolyl]ethenyl]phenylamino]-1,1-dimethyl-2-oxoethyl]benzoic acid.

EXAMPLE 34

In a manner analogous to Example 7a and 7b, when 2-(1-carboxycyclopentyl)benzoic acid methyl ester is reacted with (E)-3-[2-[4-(cyclobutyl)-2-thiazolyl]ethenyl]benzeneamine, there is obtained (E)-2-[1-[[[3-[2-[4-(cyclobutyl)-2-thiazolyl]ethenyl]phenyl]amino]carbonyl]cyclopentyl]benzoic acid methyl ester which is converted to (E)-2-[1-[[[3-[2-[4-(cyclobutyl)-2-thiazolyl]ethenyl]phenyl]amino]carbonyl]cyclopentyl]-benzoic acid.

EXAMPLE 35

| Wet Granulation Formulation | | | | |
|---|---|---|---|---|
| Ingredients | mg/tablet | | | |
| 1. (E)-2-[2-[3-[2-[4-(cyclobutyl)-2-thiazolyl]ethenyl]phenylamino]-2-oxoethyl]benzoic acid | 0.1 | 0.5 | 5.0 | 5.0 |
| 2. Lactose Anhydrous DTG | 106.9 | 106.5 | 102.0 | 118.0 |
| 3. Avicel PH 102 | 15.0 | 15.0 | 15.0 | 25.0 |
| 4. Modified Starch | 7.0 | 7.0 | 7.0 | 10.0 |
| 5. Magnesium Stearate | 1.0 | 1.0 | 1.0 | 2.0 |
| TOTAL | 130.0 | 130.0 | 130.0 | 160.0 |

Manufacturing Procedure:

1) Dissolve Item 1 in a suitable solvent such as alcohol.
2) Spread the solution in Step 1 over Item 2, dry.
3) Add Items 3 and 4 and mix for 10 minutes.
4) Add magnesium stearate and mix for 3 minutes and compress.

EXAMPLE 36

| Capsule Formulation | | | | |
|---|---|---|---|---|
| Ingredients | mg/capsule | | | |
| 1. (E)-2-[2-[3-[2-[4-(cyclobutyl)-2-thiazolyl]ethenyl]phenylamino]-2-oxoethyl]benzoic acid | 0.1 | 0.5 | 5.0 | 25.0 |
| 2. Lactose Hydrous | 168.9 | 168.5 | 159.0 | 123.0 |
| 3. Corn Starch | 20.0 | 20.0 | 25.0 | 35.0 |
| 4. Talc | 10.0 | 10.0 | 10.0 | 15.0 |
| 5. Magnesium Stearate | 1.0 | 1.0 | 1.0 | 2.0 |
| TOTAL | 200.0 | 200.0 | 200.0 | 200.0 |

Manufacturing Procedure:

1) Mix Items 1, 2 and 3 in a suitable mixer for 30 minutes.
2) Add Items 4 and 5 and mix for 3 minutes.

EXAMPLE 37

| Tablet Formulation (Wet Granulation) | | |
|---|---|---|
| | mg/tablet | |
| Item Ingredients | 100 mg | 500 mg |
| 1. (E)-2-[2-[3-[2-[4-(cyclobutyl)-2-thiazolyl]ethenyl]phenylamino]-2-oxoethyl]benzoic acid | 100 | 500 |
| 2. Lactose Anhydrous DTG | 30 | 150 |
| 3. Pregelatinized Starch | 6 | 30 |
| 4. Microcrystalline Cellulose | 30 | 150 |
| 5. Magnesium Stearate | 1 | 5 |
| TOTAL: | 167 | 835 |

Manufacturing Procedure;

1) Mix Items 1, 2, 3 and 4 and granulate with water.
2) Dry the granulation at 50° C.
3) Press the granulation through suitable milling equipment.
4) Add Item 5 and mix for three minutes; compress on a suitable press.

EXAMPLE 38

| Capsule Formulation | | | |
|---|---|---|---|
| | | mg/tablet | |
| Item | Ingredients | 100 mg | 500 mg |
| 1. | (E)-2-[2-[3-[2-[4-(cyclobutyl)-2-thiazolyl]ethenyl]phenylamino]-2-oxoethyl]benzoic acid | 100 | 500 |
| 2. | Corn Starch (Pregelatinized) | 8 | 40 |
| 3. | Modified Starch | 4 | 20 |
| 4. | Talc | 4 | 20 |
| 5. | Magnesium Stearate | 1 | 2 |
| | TOTAL: | 117 | 585 |

Manufacturing Procedure:

1) Mix Items 1, 2, and 3 and wet granulate with water.
2) Dry the granulation at 45° C. overnight.
3) Mill through a suitable screen using appropriate milling equipment.
4) Add Items 4 and 5 and mix for five minutes.

EXAMPLE 39

| Inhalation Aerosol Formulation (Suspension) | | |
|---|---|---|
| Item | Ingredients | % w/w |
| 1. | (E)-2-[2-[3-[2-[4-(cyclobutyl)-2-thiazolyl]ethenyl]phenylamino]-2-oxoethyl]benzoic acid | 1.0 |
| 2. | Sorbitan Trioleate | 0.5 |
| 3. | Freon 12 | 64.0 |
| 4. | Freon 11 | 18.5 |
| 5. | Freon 114 | 16.0 |
| | TOTAL | 100% |

Manufacturing Procedure:

1) Mix Items 1 and 2 into 4 and homogenize.
2) Fill the concentrate suspension from Step 1 into a suitable can and place in valve and crimp to seal container.
3) Pressure-fill a 80:20 mixture of Items 3 and 5.

What is claimed is:

1. A compound of the formula

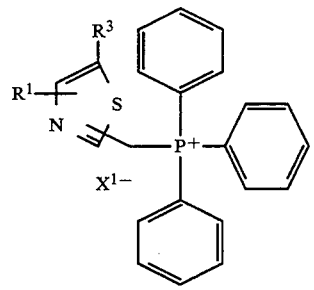

XI wherein
$R^1$ is hydrogen, alkyl, cycloalkyl, carboxyl or alkoxycarbonyl;
$R^3$ is hydrogen, alkyl or cycloalkyl and
$X^1-$ is halogen other than fluorine, provided that one of $R^1$ or $R^3$ is cycloalkyl.

2. A compound in accordance with claim 1, selected from the group consisting of [4-(cycloheptyl-2-thiazolyl)methyl]triphenyl phosphonium chloride; and [(2-cyclobutyl-4-thiazolyl)methyl]triphenyl phosphonium chloride.

3. A compound of the formula

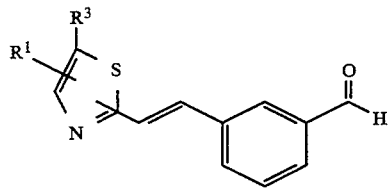

XXIII wherein
$R^1$ is hydrogen, alkyl, cycloalkyl, carboxyl or alkoxycarbonyl and
$R^3$ is hydrogen, alkyl or cycloalkyl, provided that one of $R^1$ or $R^3$ is cycloalkyl.

4. A compound in accordance with claim 3, (E)-3-[2-[4-(cyclobutyl)-2-thiazolyl]ethenyl]benzenecarboxaldehyde.

* * * * *